(12) United States Patent
Leroy

(10) Patent No.: US 8,709,734 B2
(45) Date of Patent: Apr. 29, 2014

(54) METHOD FOR IDENTIFYING MODULATORS OF GPCR GPR1 FUNCTION

(75) Inventor: Xavier Leroy, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/499,896

(22) PCT Filed: Oct. 1, 2010

(86) PCT No.: PCT/IB2010/054439
§ 371 (c)(1),
(2), (4) Date: Apr. 2, 2012

(87) PCT Pub. No.: WO2011/039731
PCT Pub. Date: Apr. 7, 2011

(65) Prior Publication Data
US 2012/0202221 A1    Aug. 9, 2012

(51) Int. Cl.
*G01N 33/53* (2006.01)
*G01N 33/566* (2006.01)
*C07K 14/705* (2006.01)

(52) U.S. Cl.
USPC .......................... 435/7.1; 436/501; 514/20.6

(58) Field of Classification Search
None
See application file for complete search history.

(56) References Cited

U.S. PATENT DOCUMENTS 7,172,876 B2 *  2/2007  Hinuma et al. .............. 435/7.21

FOREIGN PATENT DOCUMENTS

| EP | 1 514 930 | 3/2005 |
|---|---|---|
| WO | WO 2004/083867 | 9/2004 |
| WO | WO 2007/149807 | 12/2007 |

OTHER PUBLICATIONS

Barnea et al., The genetic design of signaling cascades to record receptor activation, Proc. Natl. Acad. Sci. USA, 105, 64-69, 2008.*
van Der Lee et al., β-Arrestin Recruitment Assay for the Identification of Agonists of the Sphingosine 1-Phosphate Receptor EDG1, J. Biomol. Screen. 13, 986-998, 2008.*
Arakawa T. et. al, "A Rescue Factor for Alzheimer's Diseases: Discovery, Activity, Structure, and Mechanism", Current Medicinal Chemistry, vol. 15, Sep. 2008, pp. 2086-2098.
Cole et al., "Monoclonal Antibodies and Cancer Therapy", Alan R. Liss, Inc. pp. 77-96, 1985.
Comb et al., "A Cyclic AMP- and Phorbol Ester-inducible DNA Element", Nature, 323: 353-356, 1986.
Costagliola et al., "Genetic Immunization of Outbred Mice with Thyrotropin Receptor cDNA Provides a Model of Graves' Disease", J. Clin. Invest., 105: 803-811, 2000.

Detheux et al., "Natural Proteolytic Processing of Hemofiltrate CC Chemokine 1 Generates a Potent CC Chemokine Receptor (CCR)1 and CCR5 Agonist with Anti-HIV Properties", J. Exp. Med., 192 1501-1508, 2000.
Farzan et al., "Two Orphan Seven-Transmembrane Segment Receptors Which Are Expressed in CD4-positive Cells Support Simian Immunodeficiency Virus Infection", J. Exp. Med., 186: 405-411, 1997.
Fink et al., "The CGTCA Sequence is Essential for Biological Activity of the Vasoactive Intestinal Peptide Gene cAMP-regulated Enhancer", Proc. Natl. Acad. Sci., 85: 6662-6666, 1988.
Ghattas et al., "The Encephalomyocarditis Virus Internal Ribosome Entry Site Allows Efficient Coexpression of Two Genes from a Recombinant Provirus in Cultured Cells and in Embryos", Mol. Cell. Biol., 11: 5848-5859, 1991.
Guo et al., "Humanin Peptide Suppresses Apoptosis by Interfering With Bax Activation", Nature, 420: 456-461, 2003.
Hafner, "Cytosensor Microphysiometer: Technology and Recent Applications", Biosens. Bioelectron., 15: 149-158, 2000.
Harada et al., "N-Formylated Humania Activates Both Formyl Peptide Receptor-like 1 and 2", Biochem. Biophys. Res. Comm., 324: 255-261, 2004.
Hashimoto et al., "Humanin Inhibits Neuronal Cell Death by Interacting with a Cytokine Receptor Complex or Complexes Involving CNTF Receptor a/WSX-1/gp130", Proc. Natl. Acad. Sci. USA 98: 6336-6341, 2001.
Hashimoto et al., "A Rescue Factor Abolishing Neuronal Cell Death by a Wide Spectrum of Familial Alzheimer's Disease Genes and Aβ", Mol. Biol. Cell., 20: 2864-2873, 2009.
Horton and Baxendale, "Mass Measurements of Cyclic AMP Formation by Radioimmunoassay, Enzyme Immunoassay, and Scintillation Proximity Assay", Methods Mol. Biol., 41: 91-105, 1995.
Hubbard et al., "Externally Disposed Plasma Membrane Proteins", J. Cell Biol., 64: 461-479, 1975.
Huszar et al., "Targeted Disruption of the Melanocortin-4 Receptor Results in Obesity in Mice", Cell, 88: 131-141, 1997.
Ikonen et al., "Interaction Between Alzheimer's Survival Peptide Humanin and Insulin-like Growth Factor-binding Protein 3 Regulates Cell Survival and Apoptosis", Proc. Natl. Acad. Sci. USA, 100; 13042-13047, 2003.
Jinno-Oue et al., "The Synthetic Peptide Derived from the NH2-terminal Extracellular Region of an Orphan G protein-Coupled Receptor, GPR1, Preferentially Inhibits Infection of X4 HIV1", J. Biol. Chem., 280: 30924-30934, 2005.
Jung and Van Nostrand, "Humanin Rescues Human Cerebrovascular Muscle Cells from Aβ-induced Toxicity", J. Neurochem, 84: 266-272, 2003.

(Continued)

*Primary Examiner* — Elly-Gerald Stoica
(74) *Attorney, Agent, or Firm* — Hunton & Williams LLP

(57) ABSTRACT

The invention relates to the identification of Humanin and derivatives thereof as ligands of the GPR1 GPCR (G-protein coupled receptor). The invention encompasses the use of the interaction of GPR1 polypeptides and Humanin polypeptides as the basis of screening assays for agents that modulate the activity of the GPR1 receptor. The invention also encompasses diagnostic assays based upon the GPR1/Humanin polypeptide interaction, as well as kits for performing diagnostic and screening assays.

32 Claims, 10 Drawing Sheets

(56) References Cited

OTHER PUBLICATIONS

Kariya et al., "Humanin Inhibits Cell Death of Serum-Deprived PCl2h Cells", Neuroreport, 13: 903-907, 2002.
Kariya et al., "Humanin Improves Impaired Metabolic Activity and Prolongs Survival of Serum-Deprived Human Lymphocytes", Mol. Cell Biochem., 254: 83-89, 2003.
Kenimer & Nirenberg, "Desensitization of Adenylate Cyclase to Prostaglandin $E_1$ or 2-Chroloadenosine", Mol. Pharmacol., 20: 585-591, 1981.
Kikkawa et al., "Calcium-activated, Phospholipid-dependent Protein Kinase from Rat Brain", J. Biol. Chem., 257: 13341-13348, 1982.
Kjelsberg et al., "Constitutive Activation of the $\alpha_{1B}$-Adrenergic Receptor by All Amino Acid Substitutions at a Single Site", J. Biol. Chem., 267: 1430-1433, 1992.
Kohler and Milstein, "Continuous Cultures of Fused Cells Secreting Antibody of Predefined Specificity", Nature, 256: 495-497, 1975.
Kozbor et al., "The Production of Monoclonal Antibodies from Human Lymphocytes", Immunology Today, 4: 72-79, 1983.
Mamiya and Ukai, "[$Gly^{14}$]-Humanin Improved the Learning and Memory Impairment Induced by Scopolamine in vivo", Br. J. Pharmacol. 134: 1597-1599, 2001.
McWhinney et al., "Constitutively Active Mutants of the $\alpha_{1a}$-Adrenergic Receptor Subtypes Reveal Coupling to Different Signaling Pathways and physiological Responses in Rat Cardiac Myocytes", J. Biol. Chem., 275: 2087-2097, 2000.
Mizushima and Nagata, "pEF-BOS, A Powerful Mammalian Expression Vector", Nucl. Acids Res., 18: 5322, 1990.
Montminy et al., "Identification of a Cyclic-AMP-Responsive Element Within ", Proc. Natl. Acad. Sci., 83: 6682-6686, 1986.
Ohki-Hamazaki et al., "Mice Lacking Bombesin Receptor Subtype-3 Develop Metabolic Defects and Obesity", Nature, 390: 165-168, 1997.
Parma et al., "Somatic Mutations in the Thyrotropin Receptor Gene Cause Hyperfunctioning Thyroid Adenomas", Nature, 365: 649-651, 1993.
Pinna & Ruzzene, "How Do Protein Kinases Recognize Their Substrates?", Biochem. Biophys. Acta. 1314: 191-225, 1996.
Ren et al., "Constitutively Active Mutants of the $\alpha_2$-Adrenergic Receptor", J. Biol. Chem., 268: 16483-16487, 1993.
Rudolph et al., "Expression, Characterization, and Mutagenesis of the *Yersinia pestis* Murine Toxin, a Phospholipase D Superfamily Member", J. Biol. Chem., 274: 11824-11831, 1999.
Salamon et al., "Surface Plasmon Resonance Spectroscopy Studies of Membrane Proteins: Transducin Binding and Activation by Rhodopsin Monitored in Thin Membrane Films", Biophys. J., 71: 283-294, 1996.
Salamon et al., "Plasmon Resonance Spectroscopy: Probing Molecular Interactions Within Membranes", Trends Biochem. Sci., 24: 213-219, 1999.
Salamon et al,. "Optical Anisotropy in Lipid Bilayer Membranes: Coupled Plasmon-Waveguide Resonance Measurements of Molecular Orientation, Polarizability, and Shape", Biophys. J., 80: 1557-1567, 2001.
Sarrio et al., "The Heat Shock Cognate Protein hsc73 Assembles with $A_1$ Adenosine Receptors to Form Functional Modules in the Cell Membrane", Mol. Cell. Biol., 20: 5164-5174, 2000.
Shimizu et al., "An Orphan G Protein-Coupled Receptor, GPRI, Acts as a Coreceptor to Allow Replication of Human Immunodeficiency Virus Types 1 and 2 in Brian-Derived Cells", J. Virol., 73: 5231-5239, 1999.
Shimizu et al., "A Short Amino Acid Sequence Containing Tyrosine in the N-terminal Region of G Protein-Coupled Receptors is Critical for Their Potential Use as Coreceptors for Human and Simian Immunodeficiency Viruses", J. Gen. Virol., 89: 3126-3136, 2008.
Shimizu et al., "Broad Usage Spectrum of G Protein-coupled Receptors as Coreceptors by Primary Isolates of HIV", AIDS, 23: 761-769, 2009.
Short et al., "Characterization of the Phosphoenolpyruvate Carboxykinase (GTP) Promoter-Regulatory Region", J. Biol. Chem., 261: 9721-9726, 1986.
Sponne et al., "Humanin Rescues Cortical Neurons From Prion-peptide-induced Apoptosis", Mol. Cell Neurosci, 25: 95-102, 2004.
Stables et al, "A Bioluminescent Assay for Agonist Activity at Potentially Any G-Protein-Coupled Receptor", Anal. Biochem., 252: 115-126, 1997.
Tajib et al., "Paramagnetic Proteolipsomes Containing a Pure, Native, and Oriented Seven-transmembrane Segment Protein, CCR5", Nature Biotechnology, 18: 649-654, 2000.
Tajima et al., "Evidence of in vivo Production of Humanin Peptide, a Neuroprotective Factor Against Alzheimer's Disease-Related Insults", Neurosci. Lett., 324: 227-231, 2002.
Traynor and Nahorski, "Modulation by $\mu$-Opioid Agonists of Guanosine-5'-O-(3-[$^{35}$S]thio)triphosphaste Binding to Membranes from Human Neurobalstoma SH-SY5Y Cells", Mol. Pharmacol., 47: 848-854, 1995.
Wagner et al., "Cre-mediated Gene Deletion in the Mammary Gland", Nucleic Acids Res., 25: 4323-4330, 1997.
Ying et al, "Humanin, a Newly Identified Neuroprotective Factor, Uses the G Protein-Coupled Formylpeptide Receptor-Like-1 as a Functional Receptor", J. Immunol., 172: 7078-7085, 2004.

* cited by examiner

Fig. 1 illustrates human GPR1 receptor coding region cDNA (SEQ NO: 1)

ATGGAAGATTTGGAGGAAACATTATTTGAAGAATTTGAGAACTATTCCTATGACCTAG
ACTATTACTCTCTGGAGTCTGATTTGGAGGAGAAAGTCCAGCTGGGAGTTGTTCACT
GGGTCTCCCTGGTGTTATATTGTTTGGCTTTTGTTCTGGGAATTCCAGGAAATGCCAT
CGTCATTTGGTTCACGGGGTTCAAGTGGAAGAAGACAGTCACCACTCTGTGGTTCCT
CAATCTAGCCATTGCGGATTTCATTTTTCTTCTTTCTGCCCCTGTACATCTCCTATG
TGGCCATGAATTTCCACTGGCCCTTTGGCATCTGGCTGTGCAAAGCCAATTCCTTCA
CTGCCCAGTTGAACATGTTTGCCAGTGTTTTTTTCCTGACAGTGATCAGCCTGGACCA
CTATATCCACTTGATCCATCCTGTCTTATCTCATCGGCATCGAACCCTCAAGAACTCT
CTGATTGTCATTATATTCATCTGGCTTTTGGCTTCTCTAATTGGCGGTCCTGCCCTGT
ACTTCCGGGATACTGTGGAGTTCAATAATCATACTCTTTGCTATAACAATTTTCAGAAG
CATGATCCTGACCTCACTTTGATCAGGCACCATGTTCTGACTTGGGTGAAATTTATCA
TTGGCTATCTCTTCCCTTTGCTAACAATGAGTATTTGCTACTTGTGTCTCATCTTCAAG
GTGAAGAAGCGAAGCATCCTGATCTCCAGTAGGCATTTCTGGACAATTCTGGTTGTG
GTTGTGGCCTTTGTGGTTTGCTGGACTCCTTATCACCTGTTTAGCATTTGGGAGCTCA
CCATTCACCACAATAGCTATTCCCACCATGTGATGCAGGCTGGAATCCCCCTCTCCA
CTGGTTTGGCATTCCTCAATAGTTGCTTGAACCCCATCCTTTATGTCCTAGTTAGTAA
GAAGTTCCAAGCTCGCTTCCGGTCCTCAGTTGCTGAGATACTCAAGTACACACTGTG
GGAAGTCAGCTGTTCTGGCACAGTGAGTGAACAGCTCAGGAACTCAGAAACCAAGA
ATCTGTGTCTCCTGGAAACAGCTCAATAA

Fig. 2 illustrates human GPR1 amino acid sequence (SEQ ID NO: 2).

MEDLEETLFEEFENYSYDLDYYSLESDLEEKVQLGVVHWVSLVLYCLAFVLGIPGNAIVIW
FTGFKWKKTVTTLWFLNLAIADFIFLLFLPLYISYVAMNFHWPFGIWLCKANSFTAQLNMF
ASVFFLTVISLDHYIHLIHPVLSHRHRTLKNSLIVIIFIWLLASLIGGPALYFRDTVEFNNHTLC
YNNFQKHDPDLTLIRHHVLTWVKFIIGYLFPLLTMSICYLCLIFKVKKRSILISSRHFTILVVV
VAFVVCWTPYHLFSIWELTIHHNSYSHHVMQAGIPLSTGLAFLNSCLNPILYVLISKFQARF
RSSVAEILKYTLWEVSCSGTVSEQLRNSETKNLCLLETAQ

Fig. 3 illustrates mouse GPR1 receptor coding region cDNA (SEQ NO: 3).

ATGGAAGTCTCAAAGGAAATGTTATTTGAGGAGTTGGACAACTATTCCTATGCCTTAG
ATTATTACTCCCAGGAGTCTGACCCGGAGGAGAAGGTGTACCTGGGACTCGTTCACT
GGATCTCCCTGTTCTTATATGCCCTAGCATTTGTTCTGGGCATCCCAGGAAATGCCAT
CGTCATTTGGCTCATGGGATTCAAGTGGAAGAAGACAGTCACCACTCTTTGGTTCCT
CAATCTGGCCATCGCAGACTTCATCTTTGTTCTCTTCCTGCCCCTGTACATTTCCTAC
GTGGCCTTGAGTTTCCACTGGCCCTTTGGCCTGTGGCTCTGCAAGGTTAATTCCTTC
ATTGCCCAACTGAACATGTTTTCCAGTGTTTTCTTCTTGACAGTGATCAGCCTGGACC
GCTACATCCACTTGCTCCATCCTGGCTTGTCTCATCGGCACCGGACTCTAAAGAGCT
CACTGGTTGTTGTTATACTTGTCTGGCTGTTGGCTTCTCTGCTTGGAGGTCCTACCTT
ATACTTCCGGGACACCATGGAGGTCAACAACCACATCATTTGTTATAATAATTTCCAG
GAGCATGAACTCACCTTGATGAGACACCATGTTCTGACCTGGGTGAAGTTCCTCTTT
GGCTACCTCTTCCCTTTGCTAACCATGAGCTCCTGCTACTTGTGCCTCATCTTCAAGA
TGAAAAAGCGGAACATCCTGATATCTAGAAAGCATCTCTGGATGATCCTGTCTGTGG
TCATTGCCTTCTTGGTTTGCTGGACCCCTTATCACCTGTTTAGCATCTGGGAGCTCAG
CATTCATCACAACAGCTCTTTCCAGAATGTGCTGCAGGGTGGAATCCCCCTCTCAAC
TGGCTTAGCCTTCCTCAATAGCTGCTTGAATCCCATCCTTTACGTCCTAATAAGCAAG
ACGTTCCAAGCCCGCTTCAGGGCCTCTGTTGCTGAGGTACTAAAGCGTTCGCTGTGG
GAAGCCAGCTGCTCTGGTACAGTCAGTGAACAACTCAGGAGTGCTGAAACCAAGAG
CCTGTCTCTCCTAGAAACTGCCCAGTGA

Fig. 4 illustrates mouse GPR1 amino acid sequence (SEQ ID NO: 4).

MEVSKEMLFEELDNYSYALDYYSQESDPEEKVYLGLVHWISLFLYALAFVLGIPGNAIVIW
LMGFKWKKTVTTLWFLNLAIADFIFVLFLPLYISYVALSFHWPFGLWLCKVNSFIAQLNMF
SSVFFLTVISLDRYIHLLHPGLSHRHRTLKSSLVVVILVWLLASLLGGPTLYFRDTMEVNNH
IICYNNFQEHELTLMRHHVLTWVKFLFGYLFPLLTMSSCYLCLIFKMKKRNILISRKHLWMI
LSVVIAFLVCWTPYHLFSIWELSIHHNSSFQNVLQGGIPLSTGLAFLNSCLNPILYVLISKTF
QARFRASVAEVLKRSLWEASCSGTVSEQLRSAETKSLSLLETAQ

Fig. 5 illustrates rat GPR1 receptor coding region cDNA (SEQ NO: 5).

ATGGAAGTCTCAAGGGAAATGCTATTTGAAGAACTGGACAACTACTCCTATGCCTTAG
AATATTACTCCCAGGAACCTGACGCAGAGGAGAATGTGTACCCGGGAATCGTTCACT
GGATCTCCCTGCTCTTATATGCCCTTGCGTTTGTTCTGGGAATTCCAGGGAATGCCAT
CGTCATTTGGTTCATGGGATTCAAGTGGAAGAAGACGGTCACCACTCTTTGGTTTCTC
AATCTAGCCATTGCGGATTTCATCTTTGTTCTCTTCCTGCCTCTGTATATTTCCTATGT
GGCACTGAGTTTCCACTGGCCCTTTGGGCGATGGCTCTGCAAGCTTAATTCCTTCAT
TGCCCAACTGAACATGTTTTCCAGTGTATTCTTCTTGACAGTGATTAGCCTGGACCGC
TACATTCACTTGATCCACCCTGGCTTGTCTCATCCGCACCGGACCCTGAAGAACTCA
CTGCTTGTTGTTCTATTTGTCTGGCTGTTGGCTTCTCTGCTCGGAGGTCCTACCCTGT
ACTTCCGGGACACCGTGGAGGTCAACAACCGCATTATTTGTTATAACAACTTCCAGG
AGTATGAGCTCACCCTGATGAGACACCACGTTCTGACCTGGGTGAAGTTCCTTTTTG
GCTACCTCTTGCCTTTGCTGACAATGAGCTCCTGCTACCTGTGCCTCATCTTCAAGAC
GAAGAAGCAAAACATTCTGATATCCAGTAAGCATCTCTGGATGATCCTGTCTGTGGTC
ATCGCCTTCATGGTTTGCTGGACTCCTTTTCACCTGTTCAGCATTTGGGAACTCAGCA
TTCATCACAACAGCTCTTTCCAGAACGTGCTGCAGGGCGGAATCCCTCTCTACTG
GCTTGGCCTTCCTCAATAGTTGCTTGAACCCCATCCTTTACGTTATAATAAGCAAGAA
GTTTCAAGCTCGATTCAGGGCCTCTGTTGCCGAGGTACTAAAGCGGTCACTGTGGGA
GGCCAGTTGCTCTGGTACAGTGAGTGAACAACTCAGGAGTGCTGAAACCAAGAGCC
TGTCTCTCCTAGAAACTGCCCAATGA

Fig. 6 illustrates rat GPR1 amino acid sequence (SEQ ID NO: 6).

MEVSREMLFEELDNYSYALEYYSQEPDAEENVYPGIVHWISLLLYALAFVLGIPGNAIVIW
FMGFKWKKTVTTLWFLNLAIADFIFVLFLPLYISYVALSFHWPFGRWLCKLNSFIAQLNMF
SSVFFLTVISLDRYIHLIHPGLSHPHRTLKNSLLVVLFVWLLASLLGGPTLYFRDTVEVNNRI
ICYNNFQEYELTLMRHHVLTWVKFLFGYLLPLLTMSSCYLCLIFKTKKQNILISSKHLWMIL
SVVIAFMVCWTPFHLFSIWELSIHHNSSFQNVLQGGIPLSTGLAFLNSCLNPILYVIISKKFQ
ARFRASVAEVLKRSLWEASCSGTVSEQLRSAETKSLSLLETAQ

Fig. 7 illustrates rhesus macaque GPR1 receptor coding region cDNA (SEQ NO: 7).

ATGGAAGATTTGGAGGAAACATTATTTGAAGAATTTGAAAACTATTCCTATGCCCTAG
ACTATTACTCTCTGGAGTCTGATTTGGAGGAAAAAGTCCAGCTGGGAGTTGTTCACT
GGGTCTCCCTGGTGTTATATTGTTTATCTTTTGTCCTGGGAATTCCAGGAAATGCCAT
TGTTATTTGGTTCACGGGGTTCAAGTGGAAGAAGACAGTCAGCACTCTGTGGTTCCT
CAATCTAGCCATTGCGGATTTCATCTTTCTTCTTCCTGCCCCTGTACATCTCCTATG
TGGTCATGAATTTCCACTGGCCCTTTGGCATCTGGCTGTGCAAAGCCAATTCCTTCAC
TGCCCAGTTGAACATGTTTGCCAGTGTTTTTTCCTGACAGTGATCAGTCTGGACCAC
TATATCCACTTGATCCATCCTGTCTTATCTCATCGGCATCGAACCCTCAAGAACTCTC
TGATTGTCATTATATTCATCTGGCTTTTGGCTTCTCTAATTGGCGGTCCTGCCCTATAC
TTCCGGGACACTGTGGAGTTTAATAATCATACTCTTTGCTATAACAATTTTCAGAAGCA
TGATCCTGACCTCACTGTGATCAGGCACCATGTTCTGACCTGGGTGAAATTTATTGTT
GGCTATCTCTTCCCTTTGCTAACAATGAGTATTTGCTACTTGTGTCTCATCTTCAAGGT
GAAGAAGCGAAGCATCCTGATCTCCAGTAGGCATTTCTGGACAATTCTGGCTGTGGT
TGTGGCCTTTGTGGTTTGCTGGACTCCTTATCACCTGTTTAGCATTTGGGAGCTCACC
ATTCACCACAATAGCTATTCCCACCACGTGATGCAGGCTGGAATCCCTCTCTCCACT
GGTTTGGCATTCCTCAATAGTTGCTTGAACCCCATCCTTTATGTCCTAATTAGTAAGA
AGTTCCAAGCTCGCTTCCGGTCCTCAGTTGCTGAGATACTCAAGTACACACTGTGGG
AAGTCAGCTGTTCTGGCACAGTGAGTGAACAGCTCAGGAACTCAGAAACCAAGAATC
TGTGTCTCCTGGAAACAGCCCAATAA

Fig. 8 illustrates rhesus macaque GPR1 amino acid sequence (SEQ ID NO: 8).

MEDLEETLFEEFENYSYALDYYSLESDLEEKVQLGVVHWVSLVLYCLSFVLGIPGNAIVIW
FTGFKWKKTVSTLWFLNLAIADFIFLLFLPLYISYVVMNFHWPFGIWLCKANSFTAQLNMF
ASVFFLTVISLDHYIHLIHPVLSHRHRTLKNSLIVIIFIWLLASLIGGPALYFRDTVEFNNHTLC
YNNFQKHDPDLTVIRHHVLTWVKFIVGYLFPLLTMSICYLCLIFKVKKRSILISSRHFWTILA
VVVAFVVCWTPYHLFSIWELTIHHNSYSHHVMQAGIPLSTGLAFLNSCLNPILYVLISKKFQ
ARFRSSVAEILKYTLWEVSCSGTVSEQLRNSETKNLCLLETAQ

Fig. 9 illustrates cynomolgus monkey GPR1 receptor coding region cDNA (SEQ NO: 9).

ATGGAAGATTTGGAGGAAACATTATTTGAAGAATTTGAAAACTATTCCTATGCCCTAG
ACTATTACTCTCTGGAGTCTGATTTGGAGGAAAAAGTCCAGCTGGGAGTTGTTCACT
GGGTCTCCTGGTGTTATATTGTTTATCTTTTGTCCTGGGAATTCCAGGAAATGCCAT
TGTTATTTGGTTCACCGGGTTCAAGTGGAAGAGGACAGTCAGCACTCTGTGGTTCCT
CAATCTAGCCATTGCGGATTTCATCTTTCTTCTCTTCCTGCCCCTGTACATCTCCTATG
TGGTCATGAATTTCCACTGGCCCTTTGGCATCTGGCTGTGCAAAGCCAATTCCTTCAC
TGCCCAGTTGAACATGTTTGCCAGTGTTTTTTTCCTGACAGTGATCAGTCTGGACCAC
TATATCCACTTGATCCATCCTGTCTTATCTCATCGGCATCGAACCCTCAAGAACTCTC
TGATTGTCATTATATTCATCTGGCTTTTGGCTTCTCTAATTGGTGGTCCTGCCCTATAC
TTCCGGGACACTGTGGAGTTTAATAATCATACTCTTTGCTATAACAATTTTCAGAAGCA
TGATCCCGACCTCACTGTGATCAGGCACCATGTTCTGACCTGGGTGAAATATATTGTT
GGCTATCTCTTCCCTTTGCTAACAATGAGTATTTGCTACTTGTGTCTCATCCTCAAGG
TGAAGAAGCGAAGCATCCTGATCTCCAGTAGGCATTTCTGGACAATTCTGGCTGTGG
TTGTGGCCTTTGTGGTTTGCTGGACTCCTTATCACCTGTTTAGCATTTGGGAGCTCAC
CATTCACCACAATAGCTATTCCCACCACGTGATGCAGGCTGGAATCCCTCTCTCCAC
TGGTTTGGCATTCCTCAATAGTTGCTTGAACCCCATCCTTTATGTCCTAATTAGTAAGA
AGTTCCAAGCTCGCTTCCGGTCCTCAGTTGCTGAGATACTCAAGTACACACTGTGGG
AAGTCAGCTGTTCTGGCACAGTGAGTGAACAGCTCAGGAACTCAGAAACCAAGAATC
TGTGTCTCCTGGAAACAGCCCAATAA

Fig. 10 illustrates cynomolgus monkey GPR1 amino acid sequence (SEQ ID NO: 10).

MEDLEETLFEEFENYSYALDYYSLESDLEEKVQLGVVHWVSLVLYCLSFVLGIPGNAIVI
WFTGFKWKRTVSTLWFLNLAIADFIFLLFLPLYISYVVMNFHWPFGIWLCKANSFTAQLN
MFASVFFLTVISLDHYIHLIHPVLSHRHRTLKNSLIVIIFIWLLASLIGGPALYFRDTVE
FNNHTLCYNNFQKHDPDLTVIRHHVLTWVKYIVGYLFPLLTMSICYLCLILKVKKRSILI
SSRHFWTILAVVVAFVVCWTPYHLFSIWELTIHHNSYSHHVMQAGIPLSTGLAFLNSCLN
PILYVLISKKFQARFRSSVAEILKYTLWEVSCSGTVSEQLRNSETKNLCLLETAQ

Fig. 11 illustrates human Humanin receptor coding region cDNA (SEQ NO: 11).

ATGGCTCCACGAGGGTTCAGCTGTCTCTTACTTTTAACCAGTGAAATTGACCTGCCC
GTGAAGAGGCGGGCATGA

Fig. 12 illustrates human Humanin amino acid sequence (SEQ ID NO: 12).

MAPRGFSCLLLLTSEIDLPVKRRA

Fig. 13 illustrates Gly14-Humanin amino acid sequence (SEQ ID NO: 13)

MAPRGFSCLLLLTGEIDLPVKRRA

Fig. 14 illustrated Ala8-Humanin amino acid sequence (SEQ ID NO: 14)

MAPRGFSALLLLTSEIDLPVKRRA

Fig. 15 illustrates d-Ser14-Humanin amino acid sequence (SEQ ID NO: 15)

MAPRGFSCLLLLTdSEIDLPVKRRA

Fig. 16 illustrates the effect of Humanin on the recruitment of beta-arrestin2 by GPR1.
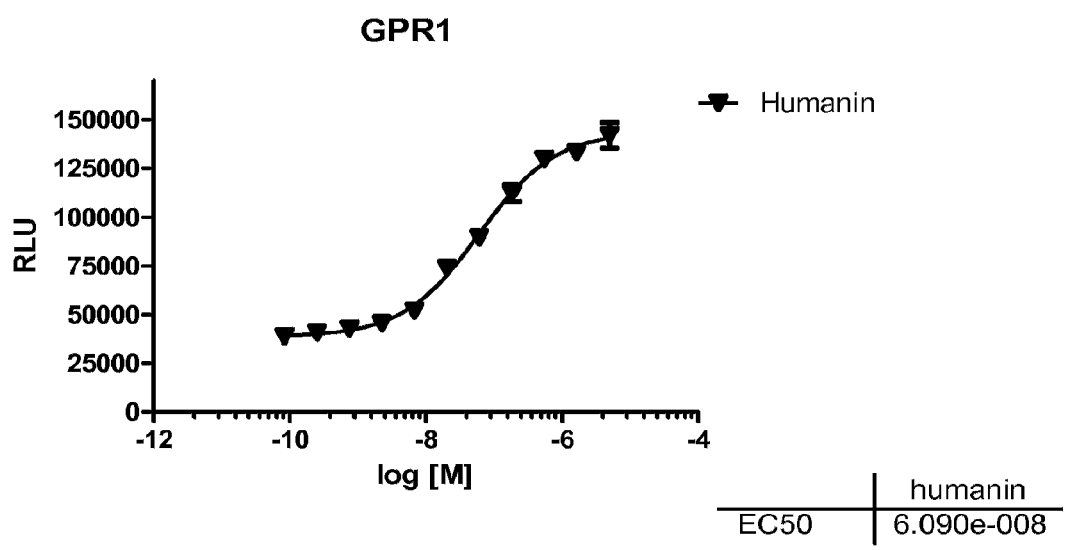

Fig. 17 illustrates the effect of Gly14-Humanin on the recruitment of beta-arrestin2 by GPR1.
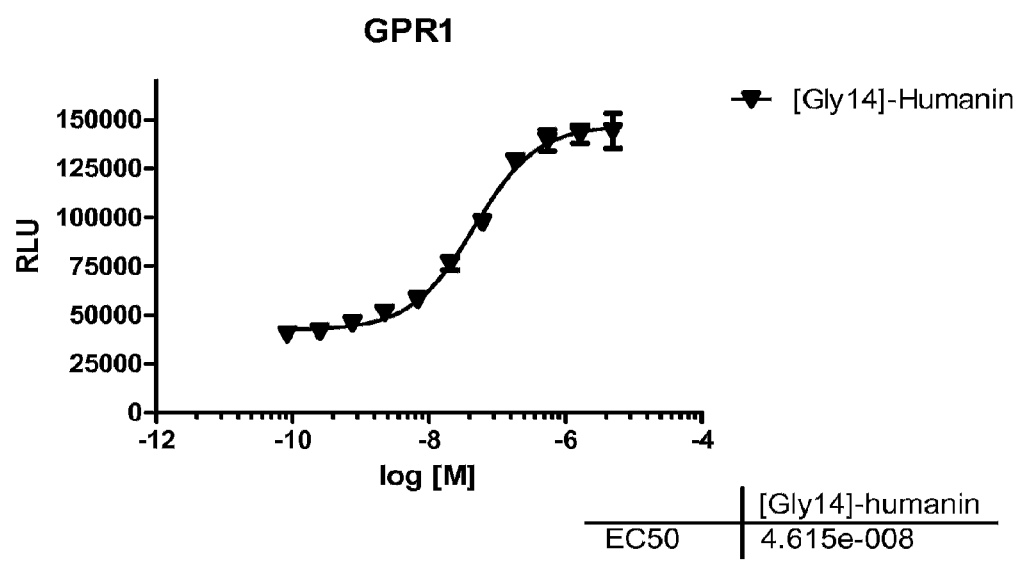

Fig. 18 illustrates the effect of d-Ser14-Humanin on the recruitment of beta-arrestin2 by GPR1.
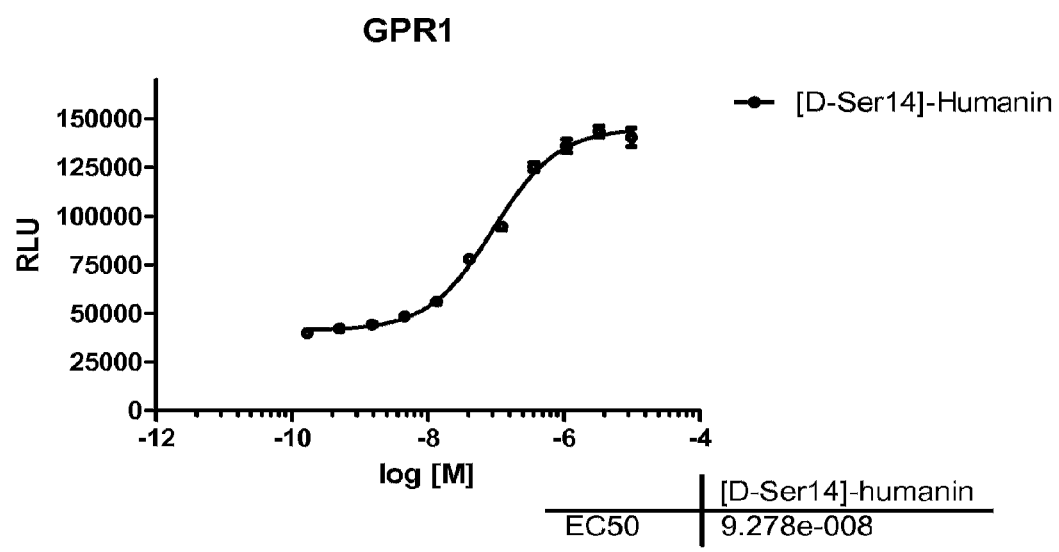

Fig. 19 illustrates the effect of Ala8-Humanin on the recruitment of beta-arrestin2 by GPR1.
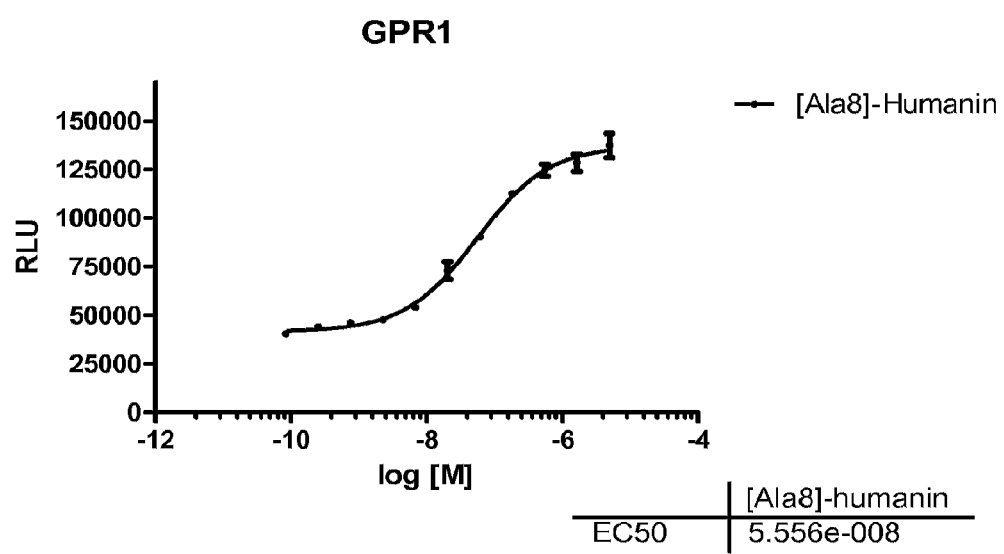

SEQUENCE LISTING

```
<160> NUMBER OF SEQ ID NOS: 15

<210> SEQ ID NO 1
<211> LENGTH: 1068
<212> TYPE: DNA
<213> ORGANISM: homo sapiens

<400> SEQUENCE: 1
atggaagatt tggaggaaac attatttgaa gaatttgaga actattccta tgacctagac      60
tattactctc tggagtctga tttggaggag aaagtccagc tgggagttgt tcactgggtc     120
tccctggtgt tatattgttt ggcttttgtt ctgggaattc caggaaatgc catcgtcatt     180
tggttcacgg ggttcaagtg gaagaagaca gtcaccactc tgtggttcct caatctagcc     240
attgcggatt tcatttttct tctctttctg cccctgtaca tctcctatgt ggccatgaat     300
ttccactggc cctttggcat ctggctgtgc aaagccaatt ccttcactgc ccagttgaac     360
atgtttgcca gtgttttttt cctgacagtg atcagcctgg accactatat ccacttgatc     420
catcctgtct tatctcatcg gcatcgaacc ctcaagaact ctctgattgt cattatattc     480
atctggcttt tggcttctct aattggcggt cctgccctgt acttccggga tactgtggag     540
ttcaataatc atactctttg ctataacaat tttcagaagc atgatcctga cctcactttg     600
atcaggcacc atgttctgac ttgggtgaaa tttatcattg gctatctctt ccctttgcta     660
acaatgagta tttgctactt gtgtctcatc ttcaaggtga agaagcgaag catcctgatc     720
tccagtaggc atttctggac aattctggtt gtggttgtgg cctttgtggt ttgctggact     780
ccttatcacc tgtttagcat ttgggagctc accattcacc acaatagcta ttcccaccat     840
```

```
gtgatgcagg ctggaatccc cctctccact ggtttggcat tcctcaatag ttgcttgaac        900
cccatccttt atgtcctagt tagtaagaag ttccaagctc gcttccggtc ctcagttgct        960
gagatactca agtacacact gtgggaagtc agctgttctg gcacagtgag tgaacagctc       1020
aggaactcag aaaccaagaa tctgtgtctc ctggaaacag ctcaataa                     1068
```

<210> SEQ ID NO 2
<211> LENGTH: 353
<212> TYPE: PRT
<213> ORGANISM: homo sapiens

<400> SEQUENCE: 2

```
Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
                20                  25                  30

Gln Leu Gly Val Val His Trp Val Ser Leu Val Leu Tyr Cys Leu Ala
            35                  40                  45

Phe Val Leu Gly Ile Pro Gly Asn Ala Ile Val Ile Trp Phe Thr Gly
        50                  55                  60

Phe Lys Trp Lys Lys Thr Val Thr Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Ala Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Ser Ile Leu Ile
225                 230                 235                 240

Ser Ser Arg His Phe Thr Ile Leu Val Val Val Ala Phe Val Val
                245                 250                 255

Cys Trp Thr Pro Tyr His Leu Phe Ser Ile Trp Glu Leu Thr Ile His
            260                 265                 270

His Asn Ser Tyr Ser His His Val Met Gln Ala Gly Ile Pro Leu Ser
        275                 280                 285

Thr Gly Leu Ala Phe Leu Asn Ser Cys Leu Asn Pro Ile Leu Tyr Val
    290                 295                 300

Leu Ile Ser Lys Phe Gln Ala Arg Phe Arg Ser Ser Val Ala Glu Ile
305                 310                 315                 320

Leu Lys Tyr Thr Leu Trp Glu Val Ser Cys Ser Gly Thr Val Ser Glu
                325                 330                 335

Gln Leu Arg Asn Ser Glu Thr Lys Asn Leu Cys Leu Leu Glu Thr Ala
```

Gln

<210> SEQ ID NO 3
<211> LENGTH: 1062
<212> TYPE: DNA
<213> ORGANISM: mouse

<400> SEQUENCE: 3

```
atggaagtct caaaggaaat gttatttgag gagttggaca actattccta tgccttagat      60
tattactccc aggagtctga cccggaggag aaggtgtacc tgggactcgt tcactggatc     120
tccctgttct tatatgccct agcatttgtt ctgggcatcc aggaaatgc catcgtcatt      180
tggctcatgg gattcaagtg gaagaagaca gtcaccactc tttggttcct caatctggcc     240
atcgcagact tcatctttgt tctcttcctg cccctgtaca tttcctacgt ggccttgagt     300
ttccactggc cctttggcct gtggctctgc aaggttaatt ccttcattgc ccaactgaac     360
atgttttcca gtgttttctt cttgacagtg atcagcctgg accgctacat ccacttgctc     420
catcctggct tgtctcatcg gcaccggact ctaaagagct cactggttgt tgttatactt     480
gtctggctgt tggcttctct gcttggaggt cctaccttat acttccggga caccatggag     540
gtcaacaacc acatcatttg ttataataat ttccaggagc atgaactcac cttgatgaga     600
caccatgttc tgacctgggt gaagttcctc tttggctacc tcttcccttt gctaaccatg     660
agctcctgct acttgtgcct catcttcaag atgaaaaagc ggaacatcct gatatctaga     720
aagcatctct ggatgatcct gtctgtggtc attgccttct tggtttgctg accccttat     780
cacctgttta gcatctggga gctcagcatt catcacaaca gctcttttcca gaatgtgctg     840
cagggtggaa tcccctctc aactggctta gccttcctca atagctgctt gaatcccatc     900
ctttacgtcc taataagcaa gacgttccaa gcccgcttca gggcctctgt tgctgaggta     960
ctaaagcgtt cgctgtggga agccagctgc tctggtacag tcagtgaaca actcaggagt    1020
gctgaaacca agagcctgtc tctcctagaa actgcccagt ga                       1062
```

<210> SEQ ID NO 4
<211> LENGTH: 353
<212> TYPE: PRT
<213> ORGANISM: mouse

<400> SEQUENCE: 4

```
Met Glu Val Ser Lys Glu Met Leu Phe Glu Glu Leu Asp Asn Tyr Ser
1               5                   10                  15

Tyr Ala Leu Asp Tyr Tyr Ser Gln Glu Ser Asp Pro Glu Glu Lys Val
            20                  25                  30

Tyr Leu Gly Leu Val His Trp Ile Ser Leu Phe Leu Tyr Ala Leu Ala
        35                  40                  45

Phe Val Leu Gly Ile Pro Gly Asn Ala Ile Val Ile Trp Leu Met Gly
    50                  55                  60

Phe Lys Trp Lys Lys Thr Val Thr Thr Leu Trp Phe Leu Asn Leu Ala
65                  70                  75                  80

Ile Ala Asp Phe Ile Phe Val Leu Phe Leu Pro Leu Tyr Ile Ser Tyr
                85                  90                  95

Val Ala Leu Ser Phe His Trp Pro Phe Gly Leu Trp Leu Cys Lys Val
            100                 105                 110

Asn Ser Phe Ile Ala Gln Leu Asn Met Phe Ser Ser Val Phe Phe Leu
        115                 120                 125
```

```
Thr Val Ile Ser Leu Asp Arg Tyr Ile His Leu Leu His Pro Gly Leu
            130                 135                 140

Ser His Arg His Arg Thr Leu Lys Ser Ser Leu Val Val Val Ile Leu
145                 150                 155                 160

Val Trp Leu Leu Ala Ser Leu Leu Gly Gly Pro Thr Leu Tyr Phe Arg
                165                 170                 175

Asp Thr Met Glu Val Asn Asn His Ile Ile Cys Tyr Asn Asn Phe Gln
            180                 185                 190

Glu His Glu Leu Thr Leu Met Arg His His Val Leu Thr Trp Val Lys
        195                 200                 205

Phe Leu Phe Gly Tyr Leu Phe Pro Leu Leu Thr Met Ser Ser Cys Tyr
210                 215                 220

Leu Cys Leu Ile Phe Lys Met Lys Lys Arg Asn Ile Leu Ile Ser Arg
225                 230                 235                 240

Lys His Leu Trp Met Ile Leu Ser Val Val Ile Ala Phe Leu Val Cys
                245                 250                 255

Trp Thr Pro Tyr His Leu Phe Ser Ile Trp Glu Leu Ser Ile His His
                260                 265                 270

Asn Ser Ser Phe Gln Asn Val Leu Gln Gly Gly Ile Pro Leu Ser Thr
            275                 280                 285

Gly Leu Ala Phe Leu Asn Ser Cys Leu Asn Pro Ile Leu Tyr Val Leu
290                 295                 300

Ile Ser Lys Thr Phe Gln Ala Arg Phe Arg Ala Ser Val Ala Glu Val
305                 310                 315                 320

Leu Lys Arg Ser Leu Trp Glu Ala Ser Cys Ser Gly Thr Val Ser Glu
                325                 330                 335

Gln Leu Arg Ser Ala Glu Thr Lys Ser Leu Ser Leu Leu Glu Thr Ala
            340                 345                 350

Gln

<210> SEQ ID NO 5
<211> LENGTH: 1062
<212> TYPE: DNA
<213> ORGANISM: rat

<400> SEQUENCE: 5
atggaagtct caagggaaat gctatttgaa gaactggaca actactccta tgccttagaa      60
tattactccc aggaacctga cgcagaggag aatgtgtacc cgggaatcgt tcactggatc     120
tccctgctct atatgccct  tgcgtttgtt ctgggaattc agggaatgc  catcgtcatt     180 tggttcatgg gattcaagtg gaagaagacg gtcaccactc tttggtttct caatctagcc     240
attgcggatt tcatctttgt tctcttcctg cctctgtata tttcctatgt ggcactgagt     300
ttccactggc cctttgggcg atggctctgc aagcttaatt ccttcattgc caactgaac     360 atgttttcca gtgtattctt cttgacagtg attagcctgg accgctacat tcacttgatc     420
caccctggct tgtctcatcc gcaccggacc ctgaagaact cactgcttgt tgttctattt     480
gtctggctgt tggcttctct gctcggaggt cctaccctgt acttccggga caccgtggag     540
gtcaacaacc gcattatttg ttataacaac ttccaggagt atgagctcac cctgatgaga     600
caccacgttc tgacctgggt gaagttcctt tttggctacc tcttgccttt gctgacaatg     660
agctcctgct acctgtgcct catcttcaag acgaagaagc aaaacattct gatatccagt     720
aagcatctct ggatgatcct gtctgtggtc atcgccttca tggtttgctg gactcctttt     780
cacctgttca gcatttggga actcagcatt catcacaaca gctctttcca gaacgtgctg     840
```

```
caggggcggaa tccctctctc tactggcttg gccttcctca atagttgctt gaaccccatc    900
ctttacgtta taataagcaa gaagtttcaa gctcgattca gggcctctgt tgccgaggta     960
ctaaagcggt cactgtggga ggccagttgc tctggtacag tgagtgaaca actcaggagt   1020
gctgaaacca agagcctgtc tctcctagaa actgcccaat ga                       1062
```

<210> SEQ ID NO 6
<211> LENGTH: 353
<212> TYPE: PRT
<213> ORGANISM: rat

<400> SEQUENCE: 6

```
Met Glu Val Ser Arg Glu Met Leu Phe Glu Glu Leu Asp Asn Tyr Ser
1               5                   10                  15

Tyr Ala Leu Glu Tyr Tyr Ser Gln Glu Pro Asp Ala Glu Glu Asn Val
            20                  25                  30

Tyr Pro Gly Ile Val His Trp Ile Ser Leu Leu Leu Tyr Ala Leu Ala
        35                  40                  45

Phe Val Leu Gly Ile Pro Gly Asn Ala Ile Val Ile Trp Phe Met Gly
    50                  55                  60

Phe Lys Trp Lys Lys Thr Val Thr Thr Leu Trp Phe Leu Asn Leu Ala
65                  70                  75                  80

Ile Ala Asp Phe Ile Phe Val Leu Phe Leu Pro Leu Tyr Ile Ser Tyr
                85                  90                  95

Val Ala Leu Ser Phe His Trp Pro Phe Gly Arg Trp Leu Cys Lys Leu
            100                 105                 110

Asn Ser Phe Ile Ala Gln Leu Asn Met Phe Ser Ser Val Phe Phe Leu
        115                 120                 125

Thr Val Ile Ser Leu Asp Arg Tyr Ile His Leu Ile His Pro Gly Leu
    130                 135                 140

Ser His Pro His Arg Thr Leu Lys Asn Ser Leu Leu Val Val Leu Phe
145                 150                 155                 160

Val Trp Leu Leu Ala Ser Leu Leu Gly Gly Pro Thr Leu Tyr Phe Arg
                165                 170                 175

Asp Thr Val Glu Val Asn Asn Arg Ile Ile Cys Tyr Asn Asn Phe Gln
            180                 185                 190

Glu Tyr Glu Leu Thr Leu Met Arg His His Val Leu Thr Trp Val Lys
        195                 200                 205

Phe Leu Phe Gly Tyr Leu Leu Pro Leu Leu Thr Met Ser Ser Cys Tyr
    210                 215                 220

Leu Cys Leu Ile Phe Lys Thr Lys Lys Gln Asn Ile Leu Ile Ser Ser
225                 230                 235                 240

Lys His Leu Trp Met Ile Leu Ser Val Val Ile Ala Phe Met Val Cys
                245                 250                 255

Trp Thr Pro Phe His Leu Phe Ser Ile Trp Glu Leu Ser Ile His His
            260                 265                 270

Asn Ser Ser Phe Gln Asn Val Leu Gln Gly Gly Ile Pro Leu Ser Thr
        275                 280                 285

Gly Leu Ala Phe Leu Asn Ser Cys Leu Asn Pro Ile Leu Tyr Val Ile
    290                 295                 300

Ile Ser Lys Lys Phe Gln Ala Arg Phe Arg Ala Ser Val Ala Glu Val
305                 310                 315                 320

Leu Lys Arg Ser Leu Trp Glu Ala Ser Cys Ser Gly Thr Val Ser Glu
                325                 330                 335

Gln Leu Arg Ser Ala Glu Thr Lys Ser Leu Ser Leu Leu Glu Thr Ala
```

Gln

<210> SEQ ID NO 7
<211> LENGTH: 1068
<212> TYPE: DNA
<213> ORGANISM: rhesus macaque

<400> SEQUENCE: 7

| | | | | | |
|---|---|---|---|---|---|
| atggaagatt | tggaggaaac | attatttgaa | gaatttgaaa | actattccta | tgccctagac | 60 |
| tattactctc | tggagtctga | tttggaggaa | aaagtccagc | tgggagttgt | tcactgggtc | 120 |
| tccctggtgt | tatattgttt | atcttttgtc | ctgggaattc | aggaaatgc | cattgttatt | 180 |
| tggttcacgg | ggttcaagtg | gaagaagaca | gtcagcactc | tgtggttcct | caatctagcc | 240 |
| attgcggatt | tcatctttct | tctcttcctg | ccctgtaca | tctcctatgt | ggtcatgaat | 300 |
| ttccactggc | cctttggcat | ctggctgtgc | aaagccaatt | ccttcactgc | ccagttgaac | 360 |
| atgtttgcca | gtgttttttt | cctgacagtg | atcagtctgg | accactatat | ccacttgatc | 420 |
| catcctgtct | tatctcatcg | gcatcgaacc | ctcaagaact | ctctgattgt | cattatattc | 480 |
| atctggcttt | tggcttctct | aattggcggt | cctgccctat | acttccggga | cactgtggag | 540 |
| tttaataatc | atactctttg | ctataacaat | tttcagaagc | atgatcctga | cctcactgtg | 600 |
| atcaggcacc | atgttctgac | ctgggtgaaa | tttattgttg | gctatctctt | cccttttgcta | 660 |
| acaatgagta | tttgctactt | gtgtctcatc | ttcaaggtga | agaagcgaag | catcctgatc | 720 |
| tccagtaggc | atttctggac | aattctggct | gtggttgtgg | cctttgtggt | ttgctggact | 780 |
| ccttatcacc | tgtttagcat | tgggagctc | accattcacc | acaatagcta | ttcccaccac | 840 |
| gtgatgcagg | ctggaatccc | tctctccact | ggtttggcat | tcctcaatag | ttgcttgaac | 900 |
| cccatccttt | atgtcctaat | tagtaagaag | ttccaagctc | gcttccggtc | ctcagttgct | 960 |
| gagatactca | agtacacact | gtgggaagtc | agctgttctg | gcacagtgag | tgaacagctc | 1020 |
| aggaactcag | aaaccaagaa | tctgtgtctc | ctggaaacag | cccaataa | | 1068 |

<210> SEQ ID NO 8
<211> LENGTH: 355
<212> TYPE: PRT
<213> ORGANISM: rhesus macaque

<400> SEQUENCE: 8

Met Glu Asp Leu Glu Glu Thr Leu Phe Glu Glu Phe Glu Asn Tyr Ser
1               5                   10                  15

Tyr Ala Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ser
        35                  40                  45

Phe Val Leu Gly Ile Pro Gly Asn Ala Ile Val Ile Trp Phe Thr Gly
    50                  55                  60

Phe Lys Trp Lys Lys Thr Val Ser Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Val Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

-continued

```
Thr Val Ile Ser Leu Asp His Tyr Ile His Leu Ile His Pro Val Leu
        130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Val Ile Arg His Val Leu Thr Trp
        195                 200                 205

Val Lys Phe Ile Val Gly Tyr Leu Phe Pro Leu Leu Thr Met Ser Ile
    210                 215                 220

Cys Tyr Leu Cys Leu Ile Phe Lys Val Lys Arg Ser Ile Leu Ile
225                 230                 235                 240

Ser Ser Arg His Phe Trp Thr Ile Leu Ala Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285

Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
        340                 345                 350

Thr Ala Gln
        355

<210> SEQ ID NO 9
<211> LENGTH: 1068
<212> TYPE: DNA
<213> ORGANISM: cynomolgus monkey

<400> SEQUENCE: 9
atggaagatt tggaggaaac attatttgaa gaatttgaaa actattccta tgccctagac        60
tattactctc tggagtctga tttggaggaa aaagtccagc tgggagttgt tcactgggtc       120
tccctggtgt tatattgttt atcttttgtc ctgggaattc aggaaatgc cattgttatt        180 tggttcaccg ggttcaagtg gaagaggaca gtcagcactc tgtggttcct caatctagcc       240
attgcggatt tcatctttct tctcttcctg cccctgtaca tctcctatgt ggtcatgaat       300
ttccactggc cctttggcat ctggctgtgc aaagccaatt ccttcactgc ccagttgaac       360
atgtttgcca gtgttttttt cctgacagtg atcagtctgg accactatat ccacttgatc       420
catcctgtct tatctcatcg gcatcgaacc ctcaagaact ctctgattgt cattatattc       480
atctggcttt tggcttctct aattggtggt cctgccctat acttccggga cactgtggag       540
tttaataatc atactctttg ctataacaat tttcagaagc atgatcccga cctcactgtg       600
atcaggcacc atgttctgac ctgggtgaaa tatattgttg ctatctcttc cctttgcta        660 acaatgagta tttgctactt gtgtctcatc ctcaaggtga agaagcgaag catcctgatc       720
tccagtaggc atttctggac aattctggct gtggttgtgg cctttgtggt ttgctggact       780
ccttatcacc tgtttagcat tgggagctca accattcacc acaatagcta tccccaccac       840
```

```
gtgatgcagg ctggaatccc tctctccact ggtttggcat tcctcaatag ttgcttgaac    900
cccatccttt atgtcctaat tagtaagaag ttccaagctc gcttccggtc ctcagttgct    960
gagatactca agtacacact gtgggaagtc agctgttctg cacagtgag  tgaacagctc   1020 aggaactcag aaaccaagaa tctgtgtctc ctggaaacag cccaataa                1068
```

<210> SEQ ID NO 10
<211> LENGTH: 355
<212> TYPE: PRT
<213> ORGANISM: cynomolgus monkey

<400> SEQUENCE: 10

```
Met Glu Asp Leu Glu Glu Thr Leu Phe Glu Glu Phe Glu Asn Tyr Ser
1               5                   10                  15

Tyr Ala Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ser
        35                  40                  45

Phe Val Leu Gly Ile Pro Gly Asn Ala Ile Val Ile Trp Phe Thr Gly
    50                  55                  60

Phe Lys Trp Lys Arg Thr Val Ser Thr Leu Trp Phe Leu Asn Leu Ala
65                  70                  75                  80

Ile Ala Asp Phe Ile Phe Leu Phe Leu Pro Leu Tyr Ile Ser Tyr
                85                  90                  95

Val Val Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Val Ile Arg His His Val Leu Thr Trp
        195                 200                 205

Val Lys Tyr Ile Val Gly Tyr Leu Phe Pro Leu Leu Thr Met Ser Ile
    210                 215                 220

Cys Tyr Leu Cys Leu Ile Leu Lys Val Lys Lys Arg Ser Ile Leu Ile
225                 230                 235                 240

Ser Ser Arg His Phe Trp Thr Ile Leu Ala Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His Val Met Gln Ala Gly Ile Pro Leu
        275                 280                 285

Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335
```

Ser Glu Gln Leu Arg Asn Ser Glu Thr Lys Asn Leu Cys Leu Leu Glu
        340                 345                 350

Thr Ala Gln
        355

<210> SEQ ID NO 11
<211> LENGTH: 75
<212> TYPE: DNA
<213> ORGANISM: homo sapiens

<400> SEQUENCE: 11
atggctccac gagggttcag ctgtctctta cttttaacca gtgaaattga cctgcccgtg      60
aagaggcggg catga                                                      75

<210> SEQ ID NO 12
<211> LENGTH: 24
<212> TYPE: PRT
<213> ORGANISM: homo sapiens

<400> SEQUENCE: 12

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 13
<211> LENGTH: 24
<212> TYPE: PRT
<213> ORGANISM: Artificial
<220> FEATURE:
<223> OTHER INFORMATION: Gly14-Humanin

<400> SEQUENCE: 13

Met Ala Pro Arg Gly Phe Ser Cys Leu Leu Leu Leu Thr Gly Glu Ile
1               5                   10                  15

Asp Leu Pro Val Lys Arg Arg Ala
            20

<210> SEQ ID NO 14
<211> LENGTH: 24
<212> TYPE: PRT
<213> ORGANISM: Artificial
<220> FEATURE:
<223> OTHER INFORMATION: Ala8-Humanin

<400> SEQUENCE: 14

Met Ala Pro Arg Gly Phe Ser Ala Leu Leu Leu Leu Thr Ser Glu Ile
1               5                   10                  15

Asp Leu Pro Val Lys Arg Arg Ala
            20

<210> SEQ ID NO 15
<211> LENGTH: 24
<212> TYPE: PRT
<213> ORGANISM: Artificial
<220> FEATURE:
<223> OTHER INFORMATION: D-Serine at Position 14

<400> SEQUENCE: 15

Met Ala Pro Arg Gly Phe Ser Ala Leu Leu Leu Leu Thr Ser Glu Ile
1               5                   10                  15

Asp Leu Pro Val Lys Arg Arg Ala
            20

METHOD FOR IDENTIFYING MODULATORS OF GPCR GPR1 FUNCTION

CROSS-REFERENCE TO RELATED APPLICATIONS

This application is the national phase application of PCT/IB2010/054439, filed Oct. 1, 2010, which claims the benefit of PCT/IB2009/054324, filed Oct. 2, 2009, the contents of each are hereby incorporated by reference in their entirety.

FIELD OF THE INVENTION

The invention relates to the identification of new ligands for the G-Protein Coupled Receptor (GPCR) GPR1 and uses thereof.

BACKGROUND OF THE INVENTION

G-protein coupled receptors (GPCRs) are proteins responsible for transducing a signal within a cell. GPCRs have usually seven transmembrane domains. Upon binding of a ligand to a portion or a fragment of a GPCR, a signal is transduced within the cell that results in a change in a biological or physiological property or behavior of the cell. GPCRs, along with G-proteins, effectors (intracellular enzymes and channels modulated by G-proteins) and beta-arrestins, are the components of a modular signaling system that connects the state of intra-cellular second messengers to extra-cellular inputs. GPCR genes and gene products can modulate various physiological processes and are potential causative agents of disease. The GPCRs seem to be of critical importance to both the central nervous system and peripheral physiological processes. The GPCR protein superfamily is represented in five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family; Family IV, the CAMP receptor family, important in the chemotaxis and development of *D. discoideum*; and Family V, the fungal mating pheromone receptor such as STE2. G proteins represent a family of heterotrimeric proteins composed of alpha, beta and gamma subunits, which bind to cell guanine nucleotides. These proteins are usually linked to cell surface receptors (receptors containing seven transmembrane domains) for signal transduction. Indeed, following ligand binding to the GPCR, a conformational-change is transmitted to the G protein, which causes the alpha-subunit to exchange a bound GDP molecule for a GTP molecule and to dissociate from the beta-gamma-subunits. The GTP-bound form of the alpha, beta and gamma-subunits typically functions as an effector-modulating moiety, leading to the production of second messengers, such as cAMP (e.g. by activation of adenyl cyclase), diacylglycerol or inositol phosphates.

Known and uncharacterized GPCRs currently constitute major targets for drug action and development. There are ongoing efforts to identify new G protein coupled receptors which can be used to screen for new agonists and antagonists having potential prophylactic and therapeutical properties. More than 300 GPCRs have been cloned to date, excluding the family of olfactory receptors. Mechanistically, approximately 50-60% of all clinically relevant drugs act by modulating the functions of various GPCRs.

GPR1 (Sequence ID Nos: 1 (human polynucleotide sequence, FIG. 1); 2 (human amino acid sequence, FIG. 2); 3 (mouse polynucleotide sequence, FIG. 3); 4 (mouse amino acid sequence, FIG. 4); 5 (rat polynucleotide sequence, FIG. 5); 6 (rat amino acid sequence, FIG. 6); 7 (rhesus macaque polynucleotide sequence, FIG. 7); 8 (rhesus macaque amino acid sequence, FIG. 8); 9 (cynomolgus monkey polynucleotide sequence, FIG. 9), and 10 (cynomolgus monkey amino acid sequence, FIG. 10)) has been described as an orphan G protein coupled receptor. The gene encoding GPR1 was assigned to the 2q33.3 region of human chromosome 2. GPR1 was tested in fusion assays for potential co-receptor activity by a range of HIV-1, HIV-2 and SIV viral strains (Farzan et al., J. Exp. Med., 186: 405-411, 1997; Shimizu et al., J. Virol., 73: 5231-5239, 1999; Shimizu et al., J. Gen. Virol., 89: 3126-3136, 2008; Shimizu et al., AIDS, 27: 761-769, 2009). Several HIV strains (GUN-$1_P$, GUN-1/A, GUN-1/S, and GUN-1/T) efficiently used GPR1 as a co-receptor. This receptor therefore appears to be a co-receptor for immunodeficiency viruses that does not belong to the chemokine receptor family. Jinno-Oue et al. (J. Biol. Chem., 280: 30924-30934, 2005) have demonstrated that a synthetic peptide derived from the NH2-terminal extracellular region of GPR1 preferentially inhibits infraction of X4 HIV1.

Humanin (HN, Sequence ID No: 12 (human Humanin amino acid sequence, FIG. 12) is a recently identified peptide with a role in neuro-protection against Alzheimer's disease (AD) associated insults (Hashimoto et al., Proc. Natl. Acad. Sci. USA 98: 6336-6341, 2001). In fact, Humanin was first identified from cDNA library of surviving neurons from an AD patient. Since then, its protective role has been described not only from various AD related insults, but also against prion-induced (Sponne et al., Mol. Cell. Neurosci. 25: 95-102, 2004) and chemical-induced damage (Mamiya and Ukai, Br. J. Pharmacol. 134: 1597-1599, 2001), thus broadening its role as a neuroprotective factor. Subsequently it has been shown to be protective against many other cytotoxic agents (Kariya et al., Mol. Cell. Biochem., 254: 83-89, 2003) and to protect non-neuronal cells such as smooth muscle cells (Jung and Van Nostrand, J. Neurochem, 82: 266-272, 2003), rat pheochromocytoma cells (Kariya et al., Neuroreport, 13: 903-907, 2002) and lymphocytes (Kariya et al., Mol. Cell. Biochem., 254: 83-89, 2003). Structurally, HN is a 24 amino acid polypeptide that is transcribed from an open reading frame within the mitochondrial 16S ribosomal RNA in mammals (Hashimoto et al., Proc. Natl. Acad. Sci. USA, 98: 6336-6341, 2001). HN is both an intracellular and secreted protein. It has been detected in normal mouse testis and colon (by immunoblot and immunohistochemical analyses using specific antibodies against HN peptide) (Tajima et al., Neurosci. Lett., 324: 227-231, 2002). So far, little has been discovered about the regulation of its production. HN promotes cell survival by binding to a variety of pro-apoptotic protein partners, such as Bax-related proteins (Guo et al., Nature, 22: 456-461, 2003), IGF binding protein-3 (IGFBP-3) (Ikonen et al., Proc. Natl. Acad. Sci. USA, 100; 13042-13047, 2003), a cytokine complex involving CNTF receptor alpha/WSX-1/gp130 (Hashimoto et al., Mol. Biol. Cell., 20: 2864-2873, 2009), but also binds and activates with high affinity and potency the G Protein coupled receptors FPRL1 (alias FPR2) and FPRL2 (alias FPR3) (Ying et al., J. Immunol., 172: 7078-7085, 2004; Harada et al., Biochem. Biophys. Res. Comm., 324: 255-261, 2004).

Methods of identifying modifiers of GPR1 activity using Chemerin or Chemerin derivatives as ligands have been described in WO 2007/149807.

SUMMARY OF THE INVENTION

The invention relates to the identification of Humanin and derivatives thereof as ligands of the GPR1GPCR (G-protein coupled receptor). The invention encompasses the use of the interaction of GPR1 polypeptides and Humanin polypeptides as the basis of screening assays for agents that modulate the activity of the GPR1 receptor. The invention also encompasses diagnostic assays based upon the GPR1/Humanin polypeptide interaction, as well as kits for performing diagnostic and screening assays.

Various embodiments of the invention are presented hereafter:

1) The present invention relates to a method of identifying an agent that modulates the function of GPR1, the method comprising: a) contacting a GPR1 polypeptide with a Humanin polypeptide in the presence and absence of a candidate modulator under conditions permitting the interaction of the Humanin polypeptide to the GPR1 polypeptide; and b) measuring the interaction of the GPR1 polypeptide to the Humanin polypeptide, wherein an increase or a decrease in interaction in the presence of the candidate modulator, relative to the interaction in the absence of the candidate modulator, identifies the candidate modulator as an agent that modulates the function of GPR1.

2) A further embodiment of the invention relates to a method of detecting the presence, in a sample, of an agent that modulates the function of GPR1, the method comprising a) contacting a GPR1 polypeptide with a Humanin polypeptide in the presence and absence of the sample under conditions permitting the interaction of the Humanin polypeptide to the GPR1 polypeptide; and b) measuring the interaction of the GPR1 polypeptide to the Humanin polypeptide, wherein an increase or a decrease in interaction in the presence of the sample, relative to the interaction in the absence of the candidate modulator, indicates the presence, in the sample of an agent that modulates the function of GPR1.

3) A further embodiment of the invention relates to a method of identifying an agent that modulates the function of GPR1, the method comprising: a) contacting a GPR1 polypeptide with a Humanin polypeptide in the presence and absence of a candidate modulator under conditions permitting the interaction of the Humanin polypeptide to the GPR1 polypeptide; and b) measuring a signaling activity of the GPR1 polypeptide, wherein a change in the activity in the presence of the candidate modulator relative to the activity in the absence of the candidate modulator identifies the candidate modulator as an agent that modulates the function of GPR1.

4) A further embodiment of the invention relates to a method of detecting the presence, in a sample, of an agent that modulates the function of GPR1, the method comprising: a) contacting a GPR1 polypeptide with a Humanin polypeptide in the presence and absence of the sample under conditions permitting the interaction of the Humanin polypeptide to the GPR1 polypeptide; b) measuring a signaling activity of the GPR1 polypeptide; and c) comparing the amount of the activity measured in a reaction containing GPR1 and Humanin polypeptide without the sample to the amount of the activity measured in a reaction containing GPR1, Humanin polypeptide and the sample, wherein a change in the activity in the presence of the sample relative to the activity in the absence of the sample indicates the presence, in the sample, of an agent that modulates the function of GPR1.

5) A further embodiment of the invention relates to a method of identifying an agent that decreases the signaling of a GPR1 polypeptide, said method comprising: a) contacting a GPR1 polypeptide with a Humanin polypeptide in the presence and absence of a candidate modulator under conditions permitting the interaction of the Humanin polypeptide to the GPR1 polypeptide; b) measuring a signaling activity of the GPR1 polypeptide in the presence and absence of the candidate modulator; and c) comparing the activity measured in the presence of the candidate modulator to the activity measured in the absence of the candidate modulator, wherein a decrease in the activity in the presence of the candidate modulator relative to the activity in the absence of the candidate modulator identifies the candidate modulator as an agent that decreases the signaling of the GPR1 polypeptide.

6) A further embodiment of the invention relates to a method according to any one of embodiments 1) to 5), wherein said agent is an antagonist.

7) A further embodiment of the invention relates to a method of identifying an agent that modulates the function of GPR1, the method comprising: a) contacting a GPR1 polypeptide with a candidate modulator; b) measuring a signaling activity of the GPR1 polypeptide in the presence of the candidate modulator; and c) comparing the activity measured in the presence of the candidate modulator to the activity measured in a sample in which the GPR1 polypeptide is contacted with a Humanin polypeptide, wherein the candidate modulator is identified as an agent that modulates the function of GPR1 when the amount of the activity measured in the presence of the candidate modulator is at least 50% of the amount induced by the Humanin polypeptide present at its $EC_{50}$.

8) A further embodiment of the invention relates to a method of detecting the presence, in a sample, of an agent that modulates the function of GPR1, the method comprising: a) contacting a GPR1 polypeptide with the sample; b) measuring a signaling activity of the GPR1 polypeptide in the presence of the sample; and c) comparing the activity measured in the presence of the sample to the activity measured in a reaction in which the GPR1 polypeptide is contacted with a Humanin polypeptide, wherein an agent that modulates the function of GPR1 is detected if the amount of the activity measured in the presence of the sample is at least 20% of the amount induced by the Humanin polypeptide present at its $EC_{50}$.

9) A further embodiment of the invention relates to a method of identifying an agent that increases the signaling of a GPR1 polypeptide, said method comprising: a) contacting a GPR1 polypeptide with a candidate modulator; b) measuring a signaling activity of the GPR1 polypeptide in the presence of the candidate modulator; and c) comparing the activity measured in the presence of the candidate modulator to the activity measured in a reaction in which the GPR1 polypeptide is contacted with a Humanin polypeptide, wherein the candidate modulator is identified as an agent that increases the signaling of GPR1 when the amount of the activity measured in the presence of the candidate modulator is at least 10% of the amount induced by the Humanin polypeptide present at its $EC_{50}$.

10) A further embodiment of the invention relates to a method according to any one of embodiments 7) to 9), wherein said Humanin polypeptide is present at about its $EC_{50}$ (and preferably at its $EC_{50}$).

11) A further embodiment of the invention relates to a method according to any one of embodiments 7) to 10), wherein said agent is an agonist.

12) A further embodiment of the invention relates to a method according to any one of embodiments 1) to 11), wherein said agent that modulates the function of GPR1 is present in a sample.

13) In a preferred embodiment according to any one of embodiments 1) to 12), the measurement is performed using a method selected from label displacement, surface plasmon resonance, fluorescence resonance energy transfer, fluorescence quenching, and fluorescence polarization (preferably from label displacement, fluorescence resonance energy transfer and fluorescence polarization and more preferably from label displacement and fluorescence resonance energy transfer).

14) A further embodiment of the invention relates to a method according to any one of embodiments 1) to 13), wherein said GPR1 polypeptide sequence is SEQ ID No. 2, and said Humanin polypeptide sequence is SEQ ID No.12, and wherein said Humanin polypeptide binds specifically to said GPR1 polypeptide.

15) A further embodiment of the invention relates to a method according to any one of embodiments 1) to 13), wherein said GPR1 polypeptide sequence is selected from the group consisting of SEQ ID No. 2, SEQ ID No. 4, SEQ ID No. 6, SEQ ID No. 8 and SEQ ID No. 10.

16) A further embodiment of the invention relates to a method according to any one of embodiments 1) to 14), wherein said GPR1 polypeptide sequence is SEQ ID No. 2.

17) A further embodiment of the invention relates to a method according to any one of embodiments 1) to 13), wherein said GPR1 polypeptide sequence is SEQ ID No. 4.

18) A further embodiment of the invention relates to a method according to any one of embodiments 1) to 13), wherein said GPR1 polypeptide sequence is SEQ ID No. 6.

19) A further embodiment of the invention relates to a method according to any one of embodiments 1) to 13), wherein said GPR1 polypeptide sequence is SEQ ID No. 8.

20) A further embodiment of the invention relates to a method according to any one of embodiments 1) to 13), wherein said GPR1 polypeptide sequence is SEQ ID No. 10.

21) A further embodiment of the invention relates to a method according to any one of embodiments 1) to 13) or 15) to 20), wherein said Humanin polypeptide sequence is selected from the group consisting of SEQ ID No.12, SEQ ID No.13, SEQ ID No.14 and SEQ ID No.15.

22) A further embodiment of the invention relates to a method according to any one of embodiments 1) to 20), wherein said Humanin polypeptide sequence is SEQ ID No.12.

23) A further embodiment of the invention relates to a method according to any one of embodiments 1) to 13) or 15) to 20), wherein said Humanin polypeptide sequence is SEQ ID No.13.

24) A further embodiment of the invention relates to a method according to any one of embodiments 1) to 13) or 15) to 20), wherein said Humanin polypeptide sequence is SEQ ID No.14.

25) A further embodiment of the invention relates to a method according to any one of embodiments 1) to 13) or 15) to 20), wherein said Humanin polypeptide sequence is SEQ ID No.15.

26) A further embodiment of the invention relates to a method according to any one of embodiments 1) to 25), wherein said Humanin polypeptide binds specifically to said GPR1 polypeptide.

27) A preferred embodiment of the invention relates to a method according to any one of embodiments 1) to 26), wherein the Humanin polypeptide is detectably labeled. It is preferred that the Humanin polypeptide is detectably labeled with a moiety selected from the group consisting of a radioisotope, a fluorophore, a quencher of fluorescence, an enzyme, an affinity tag, and an epitope tag (preferably from the group consisting of a radioisotope, a fluorophore, and an epitope tag, and more preferably from the group consisting of a radioisotope and a fluorophore).

28) A further embodiment of the invention relates to a method according to any one of embodiments 1) to 27), wherein the GPR1 polypeptide is expressed in or on a cell.

29) A further embodiment of the invention relates to a method according to any one of embodiments 1) to 28), wherein the contacting is performed in or on a cell expressing the GPR1 polypeptide.

30) A further embodiment of the invention relates to a method according to any one of embodiments 1) to 27), wherein the GPR1 polypeptide is present in a cell membrane.

31) A further embodiment of the invention relates to a method according to any one of embodiments 28) to 30), wherein said cell is selected from the group consisting of COS-7-cells, a CHO cell, a U2OS cell, a LM (TK-) cell, a NIH-3T3 cell, a HEK cell, a K-562 cell and an 1321N1 astrocytoma cell.

32) A further embodiment of the invention relates to a method according to any one of embodiments 1) to 27), wherein the GPR1 polypeptide is present in or on synthetic liposomes or virus-induced budding membranes (and preferably in or on virus-induced budding membranes).

33) A further embodiment of the invention relates to a method according to any one of embodiments 1) to 27) or 32), wherein the contacting is performed in or on synthetic liposomes (Tajib et al., Nature Biotechnology, 18: 649-654, 2000) or virus-induced budding membranes containing a GPR1 polypeptide.

34) A further embodiment of the invention relates to a method according to any one of embodiments 1) to 33), wherein the method is further performed in the presence of $G\alpha 16$.

35) A further embodiment of the invention relates to a method according to any one of embodiments 1) to 34), wherein the method is performed using a membrane fraction from cells expressing the GPR1 polypeptide.

36) A further embodiment of the invention relates to a method according to any one of embodiments 1) to 35), wherein the agent is selected from the group consisting of a peptide, a polypeptide, an antibody or antigen-binding fragment thereof, a lipid, a carbohydrate, a nucleic acid, and a small organic molecule, preferably from the group consisting of a peptide, a polypeptide, an antibody or antigen-binding fragment thereof, and a small organic molecule and more preferably from the group consisting of a peptide, a polypeptide, and a small organic molecule. Most preferably the agent is a small organic molecule.

37) A further embodiment of the invention relates to a method according to any one of embodiments 1) to 36), wherein measuring the binding to the GPR1 polypeptide comprises detecting a change in the level of a second messenger.

38) A further embodiment of the invention relates to a method according to any one of embodiments 1) to 36), wherein the step of measuring a signaling activity of the GPR1 polypeptide comprises detecting a change in the level of a second messenger.

39) A further embodiment of the invention relates to a method according to any one of embodiments 1) to 38), wherein the step of measuring a signaling activity comprises measurement of guanine nucleotide binding or exchange, adenylate cyclase activity, cAMP, beta-arrestin 1 recruitment, beta-arrestin 2 recruitment, Protein Kinase C activity, phosphatidylinositol breakdown, diacylglycerol, inositol triphosphate, intracellular calcium, arachidonic acid, MAP kinase activity, tyrosine kinase activity, or reporter gene expression.

40) In a preferred embodiment, the measuring of a signaling activity according to embodiment 39) comprises using a beta-arrestin-based assay.
41) In another preferred embodiment, the measuring of a signaling activity according to embodiment 39) comprises using a FLIPR assay or an aequorin-based assay, and preferably an aequorin-based assay.
42) A further embodiment of the invention relates to a method of diagnosing a disease or disorder characterized by dysregulation of GPR1 signaling, the method comprising: a) contacting a tissue sample with an antibody specific for a Humanin polypeptide; b) detecting binding of the antibody to the tissue sample; and c) comparing the binding detected in step (b) with a standard, wherein a difference in binding relative to the standard is diagnostic of a disease or disorder characterized by dysregulation of GPR1.
43) A further embodiment of the invention relates to a method of diagnosing a disease or disorder characterized by dysregulation of GPR1 signaling, the method comprising: a) contacting a tissue sample with an antibody specific for a GPR1 polypeptide and an antibody specific for a Humanin polypeptide; b) detecting binding of the antibodies to the tissue sample; and c) comparing the binding detected in step (b) with a standard, wherein a difference in the binding of either antibody or both, relative to the standard, is diagnostic of a disease or disorder characterized by dysregulation of GPR1.
44) A further embodiment of the invention relates to a method of diagnosing a disease or disorder characterized by dysregulation of GPR1 signaling, the method comprising: a) isolating nucleic acid from a tissue sample; b) amplifying a Humanin polynucleotide, using the nucleic acid as a template; and c) comparing the amount of amplified Humanin polynucleotide produced in step (b) with a standard, wherein a difference in the amount of amplified Humanin polynucleotide relative to the standard is diagnostic of a disease or disorder characterized by dysregulation of GPR1. In a preferred embodiment, the step of amplifying comprises RT/PCR. In another preferred embodiment, the step of comparing the amount is performed on a microarray.
45) A further embodiment of the invention relates to a method of diagnosing a disease or disorder characterized by dysregulation of GPR1 signaling, the method comprising: a) isolating nucleic acid from a tissue sample; b) amplifying a Humanin polynucleotide, using the nucleic acid as a template; and c) comparing the sequence of the amplified Humanin polynucleotide produced in step (b) with a standard, wherein a difference in the sequence, relative to the standard is diagnostic of a disease or disorder characterized by dysregulation of GPR1. In a preferred embodiment, the step of amplifying comprises RT/PCR. In another preferred embodiment, the standard is SEQ ID NO: 11. In another preferred embodiment, the step of comparing the sequence comprises minisequencing. In another preferred embodiment, the step of comparing the sequence is performed on a microarray.
46) A further embodiment of the invention relates to a composition comprising an isolated GPR1 polypeptide and an isolated Humanin polypeptide.
47) A further embodiment of the invention relates to a kit for screening for agents that modulate GPR1 signaling, or for the diagnosis of a disease or disorder characterized by dysregulation of a GPR1 polypeptide, the kit comprising an isolated GPR1 polypeptide and packaging materials therefore. In a preferred embodiment, the kit further comprises a Humanin polypeptide. Diagnostic kits according to the invention permit the determination of whether, for example, a tissue sample or an extract prepared from a tissue sample has an elevated level or activity of Humanin or GPR1. The kits may also permit the identification of mutations in genes encoding GPR1 or Humanin polypeptide and detection of an abnormal level of nucleic acids encoding GPR1 or Humanin polypeptide.

Humanin or GPR1 have an "elevated level" if the level is increased by 10% or more in a tissue sample or an extract prepared from a tissue sample in comparison to level generally observed from a similar tissue sample or from an extract prepared from a similar tissue sample.

Nucleic acids encoding GPR1 or Humanin polypeptide have "abnormal level" if the level is increased or decreased by 10% or more in comparison to level generally observed.

48) A further embodiment of the invention relates to a kit for screening for agents that modulate GPR1 signaling, or for the diagnosis of a disease or disorder characterized by dysregulation of a GPR1 polypeptide, the kit comprising an isolated polynucleotide encoding a GPR1 polypeptide and packaging materials therefore. In a preferred embodiment, the kit further comprises an isolated polynucleotide encoding a Humanin polypeptide.
49) A further embodiment of the invention relates to a kit for screening for agents that modulate GPR1 signaling, or for the diagnosis of a disease or disorder characterized by dysregulation of a GPR1 polypeptide, the kit comprising a cell transformed with a polynucleotide encoding a GPR1 polypeptide and packaging materials therefore. In a preferred embodiment, the kit further comprises an isolated polynucleotide encoding a Humanin polypeptide or a cell comprising a polynucleotide encoding a Humanin polypeptide.

As used herein, the term "GPR1 polypeptide" refers to a polypeptide having two essential properties: 1) a GPR1 polypeptide has at least 70% amino acid identity, and preferably at least 80%, more preferably at least 90%, most preferably at least 95% and notably 100% amino acid identity, to SEQ ID NO: 2; and 2) a GPR1 polypeptide has GPR1 activity, i.e., the polypeptide responds to a Humanin polypeptide or a functional fragment thereof. Optimally, a "GPR1 polypeptide" also has GPR1 signaling activity as defined herein.

As used herein, the term "GPR1 polynucleotide" refers to a polynucleotide that encodes a GPR1 polypeptide as defined herein.

As used herein, the term "GPR1 activity" refers to specific binding of a Humanin polypeptide or a functional fragment thereof by a GPR1 polypeptide.

As used herein, the term "GPR1 signaling activity" refers to the initiation or propagation of signaling by a GPR1 polypeptide. GPR1 signaling activity is monitored by measuring a detectable step in a signaling cascade by assaying one or more of the following: stimulation of GDP for GTP exchange on a G protein; recruitment of beta-arrestin1; recruitment of beta-arrestin 2; alteration of adenylate cyclase activity; protein kinase C modulation; phosphatidylinositol breakdown (generating second messengers diacylglycerol, and inositol triphosphate); intracellular calcium flux; activation of MAP kinases; modulation of tyrosine kinases; or modulation of gene or reporter gene activity. A detectable step in a signaling cascade is considered initiated or mediated if the measurable activity is altered by 10% or more above or below a baseline established in the substantial absence of a Humanin polypeptide relative to any of the GPR1 activity assays described herein below. The measurable activity can be measured directly, as in, for example, measurement of beta-arrestin recruitment. Alternatively, the measurable activity can be measured indirectly, as in, for example, a reporter gene assay.

As used herein, the term "detectable step" refers to a step that can be measured, either directly, e.g., by measurement of a second messenger or detection of a modified (e.g, phosphorylated) protein, or indirectly, e.g., by monitoring a downstream effect of that step. For example, adenylate cyclase activation results in the generation of cAMP. The activity of adenylate cyclase can be measured directly, e.g., by an assay that monitors the production of cAMP in the assay, or indirectly, by measurement of actual levels of cAMP.

As used herein, the term "isolated" refers to a population of molecules, e.g., polypeptides or polynucleotides, the composition of which is less than 50% (by weight), preferably less than 40%, more preferably less than 20% and most preferably 2% or less, contaminating molecules of an unlike nature. When the term "isolated" is applied to a GPR1 polypeptide, it is specifically meant to also encompass a GPR1 polypeptide that is associated with a lipid membrane or embedded in a lipid membrane.

As used herein, the term "Humanin polypeptide" refers to a polypeptide having at least 31% identity, and preferably at least 50%, more preferably at least 75%, most preferably at least 95% and notably 100% identity, to any of the polypeptides represented by SEQ ID NOs: 12, 13, 14 or 15 (preferably to the polypeptide represented by SEQ ID NO: 12) that specifically binds to and/or activates a signaling activity of a GPR1 polypeptide having the sequence of SEQ ID NO: 2. "Humanin polypeptide" also refers to a fragment of a polypeptide meeting the preceding definition, wherein the fragment retains at least 10% (preferably at least 50%) of the binding activity and/or level of signaling activation of the full length polypeptide of SEQ ID NO: 12. A Humanin polypeptide can comprise additions, insertions, deletions or substitutions relative to SEQ ID NO: 12, as long as the resulting polypeptide retains at least 10% (preferably at least 50%) of the binding activity and/or level of signaling activation of the full length polypeptide represented by SEQ ID NO: 12. In a preferred embodiment, the term "Humanin polypeptide" refers to a polypeptide having at least 75%, most preferably at least 95% and notably 100% identity, to the polypeptide represented by SEQ ID NO: 12 that specifically binds to and/or activates a signaling activity of a GPR1 polypeptide having the sequence of SEQ ID NO: 2. In another preferred embodiment, the term "Humanin polypeptide" refers to a polypeptide having at least 75%, most preferably at least 95% and notably 100% identity, to the polypeptide represented by SEQ ID NO: 13 that specifically binds to and/or activates a signaling activity of a GPR1 polypeptide having the sequence of SEQ ID NO: 2.

In still another preferred embodiment, the term "Humanin polypeptide" refers to a polypeptide having at least 75%, most preferably at least 95% and notably 100% identity, to the polypeptide represented by SEQ ID NO: 14 that specifically binds to and/or activates a signaling activity of a GPR1 polypeptide having the sequence of SEQ ID NO: 2.

In yet another preferred embodiment, the term "Humanin polypeptide" refers to a polypeptide having at least 75%, most preferably at least 95% and notably 100% identity, to the polypeptide represented by SEQ ID NO: 15 that specifically binds to and/or activates a signaling activity of a GPR1 polypeptide having the sequence of SEQ ID NO: 2.

The term "specifically binds" means that the Humanin polypeptide has an $EC_{50}$, or a Kd of 500 nM or less.

Derivatives may be similar polypeptides, fusion proteins or deletions thereof.

In addition to the sequences necessary for binding to GPR1 and/or activating a GPR1 signaling activity, a Humanin polypeptide, including a truncated Humanin polypeptide can comprise additional sequences, as in for example, a Humanin polypeptide fusion protein. Non-limiting examples of fusion partners include glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag).

As used herein, the term "Humanin polynucleotide" refers to a polynucleotide that encodes a Humanin polypeptide as defined herein, or the complement thereof. A "Humanin polynucleotide" may be a polynucleotide sequence which encodes truncated or modified Humanin like Gly14-Humanin, d-Ser14-Humanin or Ala8-Humanin.

The present invention also relates to an agent identified or detected by a method as described above. In addition, the present invention relates to a composition comprising said agent.

The invention further contemplates the use of an agent or a composition according to the present invention, for the preparation of a medicament for the prevention or treatment of a GPR1-related disease or a GPR1-related disorder.

Wherein said GPR1-related disease or GPR1-related disorder is chosen from the group consisting of Central Nervous System (CNS) Disorders. CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including amyotrophic lateral sclerosis (ALS), multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalami degeneration, Creutzfeld-Jakob dementia, HIV dementia, schizophrenia with dementia, and Korsakoffs psychosis are also considered to be CNS disorders. Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneo-plastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Wherein said GPR1-related disease or GPR1-related disorder is further chosen from the group consisting of inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) Further inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as conjunctivitis, keratoconjunctivitis sicca, and vernal conjunctivitis; diseases affecting the nose including allergic rhinitis; and inflammatory diseases in which autoimmune reactions are implicated or which have an autoimmune component or aetiology, such as systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, Hashimoto's thyroid and diabetes type I or II.

Wherein said GPR1-related disease or GPR1-related disorder is further chosen from the group consisting of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Wherein said GPR1-related disease or GPR1-related disorder is further chosen from the group consisting of neuroinflammation.

Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Wherein said GPR1-related disease or GPR1-related disorder is further chosen from the group consisting of immune responses.

Wherein said GPR1-related disease or GPR1-related disorder is further chosen from the group consisting of cystic fibrosis, pulmonary fibrosis, pulmonary hypertension, wound healing, diabetic nephropathy, reduction of inflammation in transplanted tissue, inflammatory diseases caused by pathogenic organisms.

Wherein said GPR1-related disease or GPR1-related disorder is further chosen from the group consisting of HIV-mediated retroviral infections.

Wherein said GPR1-related disease or GPR1-related disorder is further chosen from the group consisting of Cancer, Tumor metastasis, Ovary and uterus tumors.

Wherein said GPR1-related disease or GPR1-related disorder is further chosen from the group consisting of Female infertilities.

The invention further contemplates the use of an agent or a composition according to the present invention, for the preparation of a medicament for the prevention or treatment of a Humanin polypeptide-related disease or a Humanin polypeptide-related disorder.

Wherein said Humanin polypeptide-related disease or Humanin polypeptide-related disorder is chosen from the group consisting of Central Nervous System (CNS) Disorders. CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including amyotrophic lateral sclerosis (ALS), multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalami degeneration, Creutzfeld-Jakob dementia, HIV dementia, schizophrenia with dementia, and Korsakoffs psychosis are also considered to be CNS disorders. Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders. Pain, within the meaning of this definition, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneo-plastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Wherein said Humanin polypeptide-related disease or Humanin polypeptide-related disorder is further chosen from the group consisting of inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) Further inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as conjunctivitis, keratoconjunctivitis sicca, and vernal conjunctivitis; diseases affecting the nose including allergic rhinitis; and inflammatory diseases in which autoimmune reactions are implicated or which have an autoimmune component or aetiology, such as systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, Hashimoto's thyroid and diabetes type I or II.

Wherein said Humanin polypeptide-related disease or Humanin polypeptide-related disorder is further chosen from the group consisting of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Wherein said Humanin polypeptide-related disease or Humanin polypeptide-related disorder is further chosen from the group consisting of neuroinflammation.

Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Wherein said Humanin polypeptide-related disease or Humanin polypeptide-related disorder is further chosen from the group consisting of immune responses.

Wherein said Humanin polypeptide-related disease or Humanin polypeptide-related disorder is further chosen from the group consisting of cystic fibrosis, pulmonary fibrosis, pulmonary hypertension, wound healing, diabetic nephropathy, reduction of inflammation in transplanted tissue, inflammatory diseases caused by pathogenic organisms.

Wherein said Humanin polypeptide-related disease or Humanin polypeptide-related disorder is further chosen from the group consisting of Cancer, Tumor metastasis, Ovary and uterus tumors.

Wherein said Humanin polypeptide-related disease or Humanin polypeptide-related disorder is further chosen from the group consisting of Female infertilities.

The invention also relates to the use of a truncated and/or modified Humanin polypeptide according to the present invention or a full length Humanin polypeptide for the production of a medicament.

Said medicament may be applied for the treatment of a GPR1-related disease or a GPR1-related disorder; wherein said GPR1-related disease or GPR1-related disorder is preferentially chosen from the groups as defined above.

Said medicament may also be applied for the treatment of a Humanin polypeptide-related disease or a Humanin polypeptide-related disorder; wherein said Humanin polypeptide-related disease or Humanin polypeptide-related disorder is preferentially chosen from the groups as defined above.

As used herein, the terms "candidate compound" and "candidate modulator" refer to a compound or a composition being evaluated for the ability to modulate ligand binding to a GPR1 polypeptide or the ability to modulate an activity of a GPR1 polypeptide. Candidate modulators can be natural or synthetic compounds, including, for example, small molecules, compounds contained in extracts of animal, plant, bacterial or fungal cells, as well as conditioned medium from such cells. Preferably candidate modulators can be natural or synthetic compounds and especially small organic molecules.

As used herein, the term "small molecule" refers to a compound having molecular mass of less than 3000 Daltons, preferably less than 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" refer to an at least 10% increase or decrease in binding, or signaling activity in a given assay.

As used herein, the term "conditions permitting the binding of Humanin polypeptide to GPR1" refers to conditions of, for example, temperature, salt concentration, pH and protein concentration under which Humanin polypeptide binds GPR1. Exact binding conditions will vary depending upon the nature of the assay, for example, whether the assay uses viable cells, only membrane fraction of cells, or only protein fraction of cells.

As used herein, the term "conditions permitting the interaction of the Humanin polypeptide to the GPR1 polypeptide" refers to conditions of, for example, temperature, salt concentration, pH and protein concentration under which Humanin polypeptide binds GPR1. Exact binding conditions will vary depending upon the nature of the assay, for example, whether the assay uses viable cells, only membrane fraction of cells, or only protein fraction of cells.

As used herein, the term "sample" refers to the source of molecules being tested for the presence of an agent that modulates binding to or signaling activity of a GPR1 polypeptide.

A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a GPR1 polypeptide, a Humanin polypeptide, a nucleic acid encoding a GPR1 or Humanin polypeptide, or an agent that modifies the ligand binding and/or activity of a GPR1 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a GPR1 polypeptide. As the term is used herein, membrane fraction" is distinct from a cellular homogenate, in that at least a portion (i.e., at least 10%, preferably at least 30%, more preferably at least 60% and most preferably at least 90%) of non-membrane-associated cellular constituents has been removed. The term "membrane associated" refers to those cellular constituents that are either integrated into a lipid membrane or are physically associated with a component that is integrated into a lipid membrane.

As used herein, the term "second messenger" refers to a molecule, generated or caused to vary in concentration by the activation of a G-Protein Coupled Receptor, which participates in the transduction of a signal from that GPCR. Non-limiting examples of second messengers include cAMP, diacylglycerol, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., a Humanin polypeptide) with a receptor (e.g., GPR1). As the term is used herein, binding is "specific" if it occurs with an $EC_{50}$ or a Kd of 500 nM or less.

As used herein, the term "$EC_{50}$" refers to that concentration of an agent at which a given activity, including binding of a Humanin polypeptide or other ligand and a functional activity of a GPR1 polypeptide, is 50% of the maximum for that GPR1 activity measurable using the same assay. Stated differently, the "$EC_{50}$" is the concentration of agent that gives 50% activation, when 100% activation is set at the amount of activity that does not increase with the addition of more agonist. It should be noted that the "$EC_{50}$ of a Humanin polypeptide" will vary with the identity of the Humanin polypeptide; for example, variant Humanin polypeptides (i.e., those containing insertions, deletions, substitutions or fusions with other polypeptides, including Humanin polypeptide molecules from species other than humans and variants of them that satisfy the definition of Humanin polypeptide set forth above) can have $EC_{50}$ values higher than, lower than or the same as wild-type Humanin polypeptide. Therefore, where a Humanin polypeptide variant sequence differs from wild-type Humanin polypeptide of SEQ ID NO: 12, one of the skill in the art can determine the $EC_{50}$ for that variant according to conventional methods. The $EC_{50}$ of a given Humanin polypeptide is measured by performing an assay for an activity of a fixed amount of GPR1 polypeptide in the presence of doses of the Humanin polypeptide that increase at least until the GPR1 response is saturated or maximal, and then plotting the measured GPR1 activity versus the concentration of Humanin polypeptide.

As used herein, the term "IC50" is the concentration of an antagonist or inverse agonist that reduces the maximal activation of a GPR1 receptor by 50%.

As used herein, the term "Kd" refers to the dissociation constant. The dissociation constant has molar units (M), which correspond to the concentration of ligand at which the binding site on a particular protein is half occupied, i.e. the concentration of ligand, at which the concentration of protein with ligand bound, equals the concentration of protein with no ligand bound.

As used herein, the term "detectably labeled" refers to the property of a molecule, e.g., a Humanin polypeptide or other GPR1 ligand that has a structural modification that incorporates a functional group (label) that can be readily detected. Detectable labels include but are not limited to fluorescent compounds, isotopic compounds, chemiluminescent compounds, quantum dot labels, biotin, enzymes, electron-dense reagents, and haptens or proteins for which antisera or monoclonal antibodies are available. The various means of detection include but are not limited to spectroscopic, photochemical, radiochemical, biochemical, immunochemical, or chemical means.

As used herein, the term "affinity tag" refers to a label, attached to a molecule of interest (e.g., a Humanin polypeptide or other GPR1 ligand), that confers upon the labeled molecule the ability to be specifically bound by a reagent that binds the label. Affinity tags include, but are not limited to an epitope for an antibody (known as "epitope tags"), biotin, 6×His, and GST. Affinity tags can be used for the detection, as well as for the purification of the labeled species.

As used herein, the term "decrease in binding" refers to a decrease of at least 10% in the amount of binding detected in a given assay with a known or suspected modulator of GPR1 relative to binding detected in an assay lacking that known or suspected modulator.

As used herein, the term "delivering" when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "effective amount" refers to that amount of a drug or GPR1 modulating agent that results in a change in a GPR1 activity as defined herein (i.e., at least 10% increase or decrease in a GPR1 activity).

As used herein, the term "standard" refers to a sample taken from an individual who is not affected by a disease or disorder characterized by dysregulation of GPR1 or Humanin polypeptide activity. The "standard" is used as a reference for the comparison of GPR1 or Humanin polypeptide or mRNA levels and quality (i.e., mutant vs. wild-type), as well as for the comparison of GPR1 activities.

As used herein, the term "amplifying" when applied to a nucleic acid sequence, refers to a process whereby one or more copies of a nucleic acid sequence is generated from a template nucleic acid. A preferred method of "amplifying" is PCR or RT/PCR.

As used herein, the term "substantial absence" refers to a level of an activating or inhibiting factor that is below the level necessary to activate or inhibit GPCR function by at least 10% as measured by a given assay disclosed herein or known in the art.

As used herein, the term "G-Protein coupled receptor" or "GPCR" refers to a membrane-associated polypeptide with 7 alpha helical transmembrane domains. Functional GPCR's associate with a ligand or agonist and also associate with and activate G-proteins.

GPR1 is a GPCR.

As used herein, the term "agent that modulates the function of a GPR1 polypeptide" is a molecule or compound that increases or decreases GPR1 activity, including molecule or compound that changes the binding of Humanin polypeptides or other agonists, and/or molecule or compound that changes GPR1 downstream signaling activities.

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, F (ab) 2 fragments can be generated by treating antibody with pepsin. The resulting F (ab) 2 fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibody further comprises a label attached thereto which allows detection (e.g., the label can be a radioisotope, fluorescent compound, chemiluminescent compound, enzyme, or enzyme co-factor).

As used herein, the term "null mutation" refers to an insertion, deletion, or substitution that modifies the chromosomal sequences encoding a polypeptide, such that the polypeptide is not expressed.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

In this application the prefix "d" before the name or the respective abbreviation of an amino acid means that the amino acid has the unnatural d-configuration; for example the term "d-Ser14-Humanin" means a Humanin amino acid sequence wherein the amino acid at position 14 of natural Humanin is replaced by a Serine with d-configuration. If one-letter codes for amino acids are used, the above mentioned d-Serine is represented by "dS" as for example in SEQ ID No. 15: "MAPRGFSCLLLLTdSEIDLPVKRRA".

BRIEF DESCRIPTION OF THE FIGURES

FIG. 1 illustrates human GPR1 receptor coding region cDNA (SEQ NO: 1).

FIG. 2 illustrates human GPR1 amino acid sequence (SEQ ID NO: 2).

FIG. 3 illustrates mouse GPR1 receptor coding region cDNA (SEQ NO: 3).

FIG. 4 illustrates mouse GPR1 amino acid sequence (SEQ ID NO: 4).

FIG. 5 illustrates rat GPR1 receptor coding region cDNA (SEQ NO: 5).

FIG. 6 illustrates rat GPR1 amino acid sequence (SEQ ID NO: 6).

FIG. 7 illustrates rhesus macaque GPR1 receptor coding region cDNA (SEQ NO: 7).

FIG. 8 illustrates rhesus macaque GPR1 amino acid sequence (SEQ ID NO: 8).

FIG. 9 illustrates cynomolgus monkey GPR1 receptor coding region cDNA (SEQ NO: 9).

FIG. 10 illustrates cynomolgus monkey GPR1 amino acid sequence (SEQ ID NO: 10).

FIG. 11 illustrates human Humanin coding region cDNA (SEQ NO: 11).

FIG. 12 illustrates human Humanin amino acid sequence (SEQ ID NO: 12).

FIG. 13 illustrates Gly14-Humanin amino acid sequence (SEQ ID NO: 13).

FIG. 14 illustrates Ala8-Humanin amino acid sequence (SEQ ID NO: 14).

FIG. 15 illustrates d-Ser14-Humanin amino acid sequence (SEQ ID NO: 15).

FIG. 16 illustrates the effect of Humanin on the recruitment of beta-arrestin2 by GPR1.

FIG. 17 illustrates the effect of Gly14-Humanin on the recruitment of beta-arrestin2 by GPR1.

FIG. 18 illustrates the effect of d-Ser14-Humanin on the recruitment of beta-arrestin2 by GPR1.

FIG. 19 illustrates the effect of Ala8-Humanin on the recruitment of beta-arrestin2 by GPR1.

DETAILED DESCRIPTION OF THE INVENTION

The invention relates to the identification of Humanin polypeptides as ligands for the orphan GPR1 GPCR. These ligand-receptor interactions are useful for screening assays for agents that modulate the interaction and thus the function of GPR1. The known Humanin polypeptides and their interaction with the receptor also provide for the diagnosis of conditions involving dysregulated receptor activity.

I. Assays for the Identification of Agents that Modulate the Activity of GPR1

Agents that modulate the activity of GPR1 can be identified in a number of ways that take advantage of the interaction of the receptor with Humanin polypeptide. For example, the ability to reconstitute GPR1/Humanin polypeptide interaction either in vitro, on cultured cells or in vivo provides a target for the identification of agents that disrupt that binding. Assays based on disruption of interaction can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides, including, for example, variants of Humanin polypeptide itself.

Modulators of GPR1/Humanin polypeptide interaction can then be screened using a binding assay or a functional assay that measures downstream signaling through the receptor. Both binding assays and functional assays are validated using Humanin polypeptide.

Another approach that uses the GPR1/Humanin polypeptide interaction more directly to identify agents that modulate GPR1 function measures changes in GPR1 downstream signaling induced by candidate agents or candidate modulators. These functional assays can be performed in isolated cell membrane fractions or on cells expressing the receptor on their surfaces.

The following description provides methods for both binding and functional assays based upon the interaction of GPR1 and Humanin polypeptide.

A. GPR1 Polypeptides.

Assays using the interaction of GPR1 and Humanin polypeptide require a source of GPR1 polypeptide. The polynucleotide and polypeptide sequence of human GPR1 are presented herein as SEQ ID NOs: 1 and 2. The polynucleotide and polypeptide sequence of mouse GPR1 are presented herein as SEQ ID NOs: 3 and 4. The polynucleotide and polypeptide sequence of rat GPR1 are presented herein as SEQ ID NOs: 5 and 6. The polynucleotide and polypeptide sequence of rhesus macaque GPR1 are presented herein as SEQ ID NOs: 7 and 8. The polynucleotide and polypeptide sequence of cynomolgus monkey GPR1 are presented herein as SEQ ID NOs: 9 and 10. The polynucleotide and polypeptide sequence of human Humanin are presented herein as SEQ ID NOs: 11 and 12. Other Humanin polypeptide sequences are presented herein as SEQ ID NOs: 13-15.

GPR1 polypeptide sequence is also recorded at accession Nos. P46091, Q53TR9 and Q6NVX4 in the Swissprot database. Related sequences include those for human GPR1 (GenBank Accession Nos. NP_001091669.1 and NP_005270.2 (polypeptide sequence); GenBank Accession Nos. U13666, AC007383, BC058005, and BC067833 (nucleotide sequence)), mouse GPR1 (GenBank Accession No. BC032934 (nucleotide sequence) and Swissprot Accession No. Q8K087 (polypeptide sequence)), rat GPR1 (GenBank Accession No. S74702 (nucleotide sequence) and Swissprot Accession No. P46090 (polypeptide sequence)), rhesus macaque (GenBank Accession No. AF100204 (nucleotide sequence) and Swissprot Accession No. Q97664 (polypeptide sequence)), and Cynomolgus monkey (GenBank Accession No. AF292382 (nucleotide sequence) and Swissprot Accession No. Q95LH1 (polypeptide sequence)).

One skilled in the art can readily amplify a GPR1 sequence from a sample containing mRNA encoding the protein through basic PCR and molecular cloning techniques using primers or probes designed from the known sequences.

The expression of recombinant polypeptides is well known in the art. Those skilled in the art can readily select vectors and expression control sequences for the expression of GPR1 polypeptides useful according to the invention in eukaryotic or prokaryotic cells.

GPR1 must be associated with cell membrane or detergents like synthetic liposomes in order to have binding or signaling function. Methods for the preparation of cellular membrane fractions are well known in the art, e.g., the method reported by Hubbard and Cohn (J. Cell Biol., 64: 461-479, 1975). In order to produce membranes comprising GPR1, one need only apply such techniques to cells endogenously or recombinantly expressing GPR1. Alternatively, membrane-free GPR1 can be integrated into membrane preparations by dilution of detergent solution of the polypeptide (e.g., Salmon et al., Biophys. J., 71: 283-294, 1996).

B. Humanin Polypeptides.

Human Humanin polynucleotide and polypeptide sequences are presented herein as SEQ ID NOs: 11 and 12, respectively. Humanin polypeptide sequence is also recorded at accession No. Q8IVG9 in the Swissprot database.

Other Humanin polypeptide sequences are also presented herein as SEQ ID NOs: 13, 14 and 15.

As with GPR1, Humanin polynucleotides can be cloned through standard PCR and molecular cloning techniques using the known sequences as a source of amplification primers or probes. Similarly, cloned Humanin polypeptides can be expressed in eukaryotic or prokaryotic cells as known in the art. As a non-limiting example, a mammalian Humanin expression vector system can comprise a bicistronic expression vector containing the promoter of human EFIa (described by Mishizuma and Nagata, Nucl. Acids Res., 18: 5322, 1990), a polylinker, the ECMV internal ribosome entry site (IRES, described by Ghattas et al., Mol. Cell. Biol., 11: 5848-5859, 1991) and the neomycin resistance gene followed by an SV40 polyA signal. Humanin polypeptide can also be expressed in vitro through in vitro transcription and translation.

Further, if desired for a given assay or technique, Humanin polypeptides useful according to the invention can be produced as fusion proteins or tagged proteins. For example, either full length Humanin polypeptide or a portion thereof (i.e., at least 10 amino acids, preferably at least 20 amino acids or more, up to one amino acid less than full length Humanin polypeptide) can be fused to Glutathione-S-Transferase (GST), secreted alkaline phosphatase (SEAP), a FLAG tag, a Myc tag, or a 6×-His peptide to facilitate the purification or detection of the Humanin polypeptide. Methods and vectors for the production of tagged or fusion proteins are well known in the art, as are methods of isolating and detecting such fused or tagged proteins.

Humanin polypeptides and particularly truncated forms can also be prepared by chemical synthesis as known in the art.

Recombinant Humanin polypeptides can be used in purified form. Alternatively, conditioned medium from Humanin transfected cells can be used. The amounts of Humanin necessary in a given binding or functional assay according to the invention will vary depending upon the assay. The affinities and $EC_{50}$ values of tagged Humanin polypeptides for GPR1 may vary relative to those of full length wild type Humanin polypeptide, and the amount necessary for a given assay can therefore be adjusted relative to the wild-type values. If necessary for a given assay, Humanin polypeptides can be labeled by incorporation of radiolabeled amino acids in the medium during synthesis, e. g., $^{35}$S-labeled amino acids like $^{35}$S-Met, $^{14}$C-labeled amino acids like $^{14}$C-Leu, $^{3}$H-labeled (tritiated) amino acids, or others as appropriate. Methods of chemical labeling are known in the art.

Fluorescent labels can also be attached to Humanin polypeptides or to other GPR1 ligands using standard labeling techniques.

C. Assays to Identify Modulators of GPR1Activity

The identification of Humanin polypeptides as ligands of the GPR1 receptor permits screening assays to identify agonists, antagonists and inverse agonists of receptor activity. The screening assays will have two general approaches.

1) Ligand binding assays, in which cells expressing GPR1, membrane extracts from such cells, or immobilized lipid membranes comprising GPR1 are exposed to a labeled Humanin polypeptide and candidate compound. Following incubation, the reaction mixture is measured for specific binding of the labeled Humanin polypeptide to the GPR1 receptor. Compounds that interfere with or displace labeled Humanin polypeptide can be agonists, antagonists or inverse agonists of GPR1 activity. Functional analysis can be performed on positive compounds to determine which of these categories they fit.

2) Functional assays, in which a signaling activity of GPR1 is measured. a) For agonist screening, cells expressing GPR1 or membranes prepared from them are incubated with candidate compound, and a signaling activity of GPR1 is measured. The assays are validated using a Humanin polypeptide as agonist, and the activity induced by compounds that modulate receptor activity is compared to that induced by Humanin polypeptide. An agonist or partial agonist will have a maximal biological activity corresponding to at least 10% of the maximal activity of wild type Humanin polypeptide when the agonist or partial agonist is present, and preferably will have 50%, 75%, 100% or more, including 2-fold, 5-fold, 10-fold or more activity than wild-type human Humanin polypeptide. b) For antagonist or inverse agonist screening, cells expressing GPR1 or membranes isolated from them are assayed for signaling activity in the presence of a Humanin polypeptide with or without a candidate compound. Antagonists or inverse agonists will reduce the level of Humanin polypeptide-stimulated receptor activity by at least 10%, relative to reactions lacking the antagonist or inverse agonist. c) For inverse agonist screening, cells expressing constitutive GPR1 activity or membranes isolated from them are used in a functional assay that measures an activity of the receptor in the presence and absence of a candidate compound. Inverse agonists are those compounds that reduce the constitutive activity of the receptor by at least 10%. Overexpression of GPR1 (i.e., expression of 5-fold or higher excess of GPR1 polypeptide relative to the level naturally expressed in cells in vivo) may lead to constitutive activation. GPR1 can be overexpressed by placing it under the control of a strong constitutive promoter, e.g., the CMV early promoter. Alternatively, certain mutations of conserved GPCR amino acids or amino acid domains tend to lead to constitutive activity (Kjelsberg et al., J. Biol. Chem., 267: 1430-1433, 1992; McWhinney et al., J. Biol. Chem., 275: 2087-2097, 2000; Ren et al., J. Biol. Chem., 268: 16483-16487, 1993; and Parma et al., Nature, 365: 649-651, 1993).

Ligand binding and displacement assays: One can use GPR1 polypeptides expressed on a cell, or isolated membranes containing receptor polypeptides, along with a Humanin polypeptide in order to screen for compounds that inhibit the binding of Humanin polypeptide to GPR1. When identified in an assay that measures binding or Humanin polypeptide displacement alone, compounds will have to be subjected to functional testing to determine whether they act as agonists, antagonists or inverse agonists.

For displacement experiments, cells expressing a GPR1 polypeptide are incubated in binding buffer with labeled Humanin polypeptide in the presence or absence of increasing concentrations of a candidate modulator. To validate and calibrate the assay, control competition reactions using increasing concentrations of unlabeled Humanin polypeptide can be performed. After incubation, cells are washed extensively, and bound, labeled Humanin polypeptide is measured as appropriate for the given label (e.g., scintillation counting, enzyme assay, fluorescence, etc.). A decrease of at least 10% in the amount of labeled Humanin polypeptide bound in the presence of candidate modulator indicates displacement of binding by the candidate modulator. Candidate modulators are considered to bind specifically in this or other assays described herein if they displace 50% of labeled Humanin polypeptide (sub-saturating Humanin polypeptide dose).

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of a Humanin polypeptide from the aqueous phase to a GPR1 polypeptide immobilized in a membrane on the sensor. This change in mass is measured as resonance units versus time after injection or removal of the Humanin polypeptide or candidate modulator and can be measured using for instance a Biacore Biosensor (Biacore AB). GPR1 can be immobilized on a sensor chip (for example, research grade CM5 chip; Biacore AB) in a thin film lipid membrane according to methods described by Salmon et al. (Biophys J. 71: 283-294; Biophys. J., 80: 1557-1567, 2001; Trends Biochem. Sci., 24: 213-219, 1999). Sarrio et al. (Mol. Cell. Biol., 20: 5164-5174, 2000) demonstrated that SPR can be used to detect ligand binding to the GPCR A (1) adenosine receptor immobilized in a lipid layer on the chip. Conditions for Humanin polypeptide binding to GPR1 in an SPR assay can be fine-tuned by one of skill in the art using as a starting point the conditions reported by Sarrio et al. (Mol. Cell. Biol., 20: 5164-5174, 2000).

SPR can assay for modulators of binding in at least two ways. First, a Humanin polypeptide can be pre-bound to immobilized GPR1 polypeptide, followed by injection of candidate modulator at approximately 10 µl/min flow rate and a concentration ranging from 1 nM to 100 µM. Displacement of the bound Humanin polypeptide can be quantified, permitting detection of modulator binding. Alternatively, the membrane-bound GPR1 polypeptide can be pre-incubated with candidate modulator and challenged with a Humanin polypeptide. A difference in Humanin polypeptide binding to the GPR1 exposed to modulator relative to that on a chip not pre-exposed to modulator will demonstrate binding. In either assay, a decrease of 10% or more in the amount of a Humanin polypeptide bound in the presence of candidate modulator, relative to the amount of a Humanin polypeptide bound in the absence of candidate modulator, indicates that the candidate modulator inhibits the interaction of GPR1 and Humanin polypeptide.

Another method of measuring inhibition of binding of a Humanin polypeptide to GPR1 uses fluorescence resonance energy transfer (FRET). FRET is a quantum mechanical phenomenon that occurs between a fluorescence donor (D) and a fluorescence acceptor (A) in close proximity to each other (usually <100 Angström of separation) if the emission spectrum of D overlaps with the excitation spectrum of A. The molecules to be tested, e.g., a Humanin polypeptide and a GPR1 polypeptide, are labeled with a complementary pair of donor and acceptor fluorophores. While bound closely together by the GPR1-Humanin polypeptide interaction, the fluorescence emitted upon excitation of the donor fluorophore will have a different wavelength than that emitted in response to that excitation wavelength when the polypeptides are not bound, providing for quantification of bound versus unbound polypeptides by measurement of emission intensity at each wavelength. Donor: Acceptor pairs of fluorophores with which to label the polypeptides are well known in the art. Of particular interest are variants of the A. victoria GFP known as Cyan FP (CFP, Donor (D)) and Yellow FP (YFP, Acceptor (A)). The GFP variants can be made as fusion proteins with the respective members of the binding pair to serve as D-A pairs in a FRET scheme to measure protein-protein interaction. Vectors for the expression of GFP variants as fusions are known in the art. As an example, a CFP-Humanin polypeptide fusion and a YFP-GPR1 fusion can be made. The addition of a candidate modulator to the mixture of labeled Humanin polypeptide and GPR1 proteins will result in an inhibition of energy transfer evidenced by, for example, a decrease in YFP fluorescence relative to a sample without the candidate modulator.

In an assay using FRET for the detection of GPR1-Humanin polypeptide interaction, a 10% or greater decrease in the intensity of fluorescent emission at the acceptor wavelength in samples containing a candidate modulator, relative to samples without the candidate modulator, indicates that the candidate modulator inhibits GPR1-Humanin polypeptide interaction.

A variation of FRET uses fluorescence quenching to monitor molecular interactions: One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labeled GPR1 polypeptide is indicative that the Humanin polypeptide bearing the quencher has been displaced. For quenching assays, a 10% or greater increase in the intensity of fluorescent emission in samples containing a candidate modulator, relative to samples without the candidate modulator, indicates that the candidate modulator inhibits GPR1-Humanin polypeptide interaction.

In addition to the surface plasmon resonance and FRET methods, fluorescence polarization measurement is useful to quantitate protein-protein binding. The fluorescence polarization value for a fluorescently-tagged molecule depends on the rotational correlation time or tumbling rate. Protein complexes, such as those formed by GPR1 associating with a fluorescently labeled Humanin polypeptide, have higher polarization values than uncomplexed, labeled Humanin polypeptide. The inclusion of a candidate inhibitor of the GPR1-Humanin polypeptide interaction results in a decrease in fluorescence polarization, relative to a mixture without the candidate inhibitor, if the candidate inhibitor disrupts or inhibits the interaction of GPR1 with Humanin polypeptide. Fluorescence polarization is well suited for the identification of small molecules that disrupt the formation of polypeptide or protein complexes. A decrease of 10% or more in fluorescence polarization in samples containing a candidate modulator, relative to fluorescence polarization in a sample lacking the candidate modulator, indicates that the candidate modulator inhibits GPR1-Humanin polypeptide interaction.

Another alternative for monitoring GPR1-Humanin polypeptide interactions uses a biosensor assay.

ICS biosensors have been described by AMBRI (Australian Membrane Biotechnology Research Institute). In this technology, the association of macromolecules such as GPR1 and Humanin polypeptide, is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of GPR1 and Humanin polypeptide.

It is important to note that in assays of protein-protein interaction, it is possible that a modulator of the interaction need not necessarily interact directly with the domain(s) of the proteins that physically interact. It is also possible that a modulator will interact at a location removed from the site of protein-protein interaction and cause, for example, a conformational change in the GPR1 polypeptide. Modulators (inhibitors or agonists) that act in this manner are nonetheless of interest as agents to modulate the activity of GPR1.

Any of the binding assays described can be used to determine the presence of an agent in a sample, e.g., a tissue sample, that binds to the GPR1 receptor molecule, or that affects the binding of Humanin polypeptide to the receptor. To do so, GPR1 polypeptide is reacted with Humanin polypeptide or another ligand in the presence or absence of the sample, and Humanin polypeptide or ligand binding is measured as appropriate for the binding assay being used. A decrease of 10% or more in the binding of Humanin polypeptide or other ligand indicates that the sample contains an agent that modulates GPR1 or ligand binding to the receptor polypeptide.

Functional Assays of Receptor Activity i. GTPase/GTP Binding Assays:

For GPCRs such as GPR1, a measure of receptor activity is the binding of GTP by cell membranes containing receptors. In the method described by Traynor and Nahorski (Mol. Pharmacol., 47: 848-854, 1995), one essentially measures G-protein coupling to membranes by measuring the binding of labeled GTP. For GTP binding assays, membranes isolated from cells expressing the receptor could be incubated in a buffer containing inter alia $^{35}$S-GTP-gamma-S and GDP. After incubation unbound labeled GTP would be removed by filtration. Bound, labeled GTP would be measured by liquid scintillation counting.

In order to assay for modulation of Humanin polypeptide-induced GPR1 activity, membranes prepared from cells expressing a GPR1 polypeptide would be mixed with a Humanin polypeptide, and the GTP binding assay would be performed in the presence and absence of a candidate modulator of GPR1 activity. A decrease of 10% or more in labeled GTP binding as measured by scintillation counting in an assay of this kind containing candidate modulator, relative to an assay without the modulator, indicates that the candidate modulator inhibits GPR1 activity.

A similar GTP-binding assay can be performed without Humanin polypeptide to identify compounds that act as agonists. In this case, Humanin polypeptide-stimulated GTP binding is used as a standard. A compound is considered an agonist if it induces at least 50% of the level of GTP binding induced by Humanin polypeptide when the compound is present at 10 uM or less, and preferably will induce a level the same as or higher than that induced by Humanin polypeptide.

GTPase activity is measured by incubating the membranes containing a GPR1 polypeptide with gamma-$^{32}$P-GTP. Active GTPase will release the label as inorganic phosphate, which is detected after separation by scintillation counting. Controls include assays using membranes isolated from cells not expressing GPR1 (mock-transfected), in order to exclude possible non-specific effects of the candidate compound.

In order to assay for the effect of a candidate modulator on GPR1-regulated GTPase activity, membrane samples are incubated with a Humanin polypeptide, with and without the modulator, followed by the GTPase assay. A change (increase or decrease) of 10% or more in the level of GTP binding or GTPase activity relative to samples without modulator is indicative of GPR1 modulation by a candidate modulator.

ii. Downstream Pathway Activation Assays:

a. Calcium flux—The Aequorin-based Assay:

The aequorin assay takes advantage of the responsiveness of mitochondrial apoaequorin to intracellular calcium release induced by the activation of GPCRs (Stables et al, Anal. Biochem., 252: 115-126, 1997; Detheux et al., J. Exp. Med., 192 1501-1508, 2000). Briefly, GPR1-expressing clones are transfected to coexpress mitochondrial apoaequorin and Gα16. Cells are incubated with Coelenterazine H (Molecular Probes), washed (e.g. in DMEM-F12 culture medium) and resuspended at a defined concentration (e.g. around 0.5×10$^6$ cells/ml). Cells are then mixed with test agonist peptides and light emission by the aequorin is recorded with a luminometer. Results are expressed as Relative Light Units (RLU). Controls include assays using membranes isolated from cells not expressing GPR1 (mock-transfected), in order to exclude possible non-specific effects of the candidate compound.

Aequorin activity or intracellular calcium levels are "changed" if light intensity increases or decreases by 10% or more in a sample of cells, expressing a GPR1 polypeptide and treated with a candidate modulator, relative to a sample of cells expressing the GPR1 polypeptide but not treated with the candidate modulator or relative to a sample of cells not expressing the GPR1 polypeptide (mock-transfected cells) but treated with the candidate modulator.

When performed in the absence of a Humanin polypeptide, the assay can be used to identify an agonist of GPR1 activity. When the assay is performed in the presence of a Humanin polypeptide, it can be used to assay for an antagonist or an allosteric modulator.

b. Adenylate Cyclase Assay:

Assays for adenylate cyclase activity are described by Kenimer & Nirenberg (Mol. Pharmacol., 20: 585-591, 1981).

According to the invention, adenylate cyclase activity is "changed" if it increases or decreases by 10% or more in a sample taken from cells treated with a candidate modulator of GPR1 activity, relative to a similar sample of cells not treated with the candidate modulator or relative to a sample of cells not expressing the GPR1 polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton and Baxendale (Methods Mol. Biol., 41: 91-105, 1995), describe an RIA for cAMP. A number of kits for the measurement of cAMP are commercially available. Control reactions should be performed using extracts of mock-transfected cells to exclude possible non-specific effects of some candidate modulators.

The level of cAMP is "changed" if the level of cAMP detected in cells, expressing a GPR1 polypeptide and treated with a candidate modulator of GPR1 activity (or in extracts of such cells), using the RIA-based assay of Horton and Baxendale (Methods Mol. Biol., 41: 91-105, 1995), increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of GPR1 by monitoring phospholipid breakdown, and the resulting production of second messengers DAG and/or inositol triphosphate (IP3). Methods of measuring each of these are described in Phospholipid Signaling Protocols, edited by Ian M. Bird. Totowa, N.J., Humana Press, 1998. See also Rudolph et al. (J. Biol. Chem., 274: 11824-11831, 1999) which also describes an assay for phosphatidylinositol breakdown. Assays should be performed using cells or extracts of cells expressing GPR1, treated or not treated with a Humanin polypeptide with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a GPR1 polypeptide and treated with a candidate modulator, relative to the level observed in a sample from cells expressing a GPR1 polypeptide that is not treated with the candidate modulator.

e. PKC Activation Assays:

Growth factor receptor tyrosine kinases tend to signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below. For a more direct measure of PKC activity, the method of Kikkawaet al. (J. Biol. Chem., 257: 13341, 1982) can be used. This assay measures phosphorylation of a PKC substrate peptide, which is subsequently separated by binding to phosphocellulose paper. This PKC assay system can be used to measure activity of purified kinase, or the activity in crude cellular extracts.

In one possible assay, the substrate is the peptide Ac-FKKSFKL-NH2, derived from the myristoylated alaninerich protein kinase C substrate protein (MARCKS). The $K_m$ of the enzyme for this peptide is approximately 50 μM. Other basic, protein kinase C-selective peptides known in the art can also be used, at a concentration of at least 2-3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PCK present (non-activating conditions). For most purposes according to the invention, non-activating conditions will be used, such that the PKC that is active in the sample when it is isolated is measured, rather than measuring the PKC that can be activated. For non-activating conditions, calcium is omitted in the assay in favor of EGTA. The assay is performed in a mixture containing HEPES, DTT, $MgCl_2$, ATP, gamma-32P-ATP, peptide substrate, phosphatidylserine/diacylglycerol membranes, and calcium (or EGTA). Reactions are performed at the appropriate temperature (e.g. around 30° C.) for the appropriate time (e.g. 5-10 minutes), followed by addition of ATP and EDTA, which stops the reactions.

After the reaction is stopped, a portion of each reaction is spotted onto a Whatman P81 cellulose phosphate filter, followed by washes with diluted phosphoric acid and finally with 95% EtOH.

Bound radioactivity is measured by scintillation counting. Specific activity (cpm/nmol) of the labeled ATP is determined by spotting a sample of the reaction onto P81 paper and counting without washing. Units of PKC activity are defined as nmol phosphate transferred per min.

An alternative assay can be performed using a Protein Kinase C Assay Kit sold by PanVera.

Assays might be performed on extracts from cells expressing a GPR1 polypeptide, treated or not treated with a Humanin polypeptide with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing GPR1 and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat #9820) or the Flash Plate MAP Kinase assays sold by Perkin-Elmer Life Sciences.

MAP Kinase activity is "changed" if the level of activity is increased or decreased by 10% or more in a sample from cells, expressing a GPR1 polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr kinases). Kinase assays can be performed with both purified kinases and crude extracts prepared from cells expressing a GPR1 polypeptide, treated with or without a Humanin polypeptide, with or without a candidate modulator. Control reactions should be performed using mock-transfected cells, or extracts from them in order to exclude possible non-specific effects of some candidate modulators. Substrates can be either full length protein or synthetic peptides representing the substrate. Pinna & Ruzzene (Biochem. Biophys. Acta. 1314: 191-225, 1996; incorporated herein by reference) list a number of phosphorylation substrate sites useful for measuring kinase activities. A number of kinase substrate peptides are commercially available. One that is particularly useful is the commercially available "Src-related peptide" RRLIEDAEYAARG, which is a substrate for many receptor and nonreceptor tyrosine kinases. Because the assay described below requires binding of peptide substrates to filters, the peptide substrates should have a net positive charge to facilitate binding.

Generally, peptide substrates should have at least 2 basic residues and a free amino terminus.

Assays are generally carried out in an appropriate volume comprising kinase buffer (BSA, Tris-Cl, $MgCl_2$; depending upon the exact kinase assayed for, $MnCl_2$ can be used in place of or in addition to the $MgCl_2$), ATP, 32P-ATP, peptide substrate, cell extract containing kinase to be tested (cell extracts used for kinase assays should contain a phosphatase inhibitor like sodium orthovanadate), and $H_2O$. Reactions are performed at around 30° C., and are initiated by the addition of the cell extract.

Kinase reactions are performed for 30 seconds to about 30 minutes, followed by the addition of diluted, cold trichloroacetic acid (TCA). Samples are spun in a microcentrifuge, and a fraction of the supernatant is spotted onto Whatman P81 cellulose phosphate filter circles. The filters are washed with diluted phosphoric acid, followed by acetone. Filters are dried and incorporated 32P is measured by scintillation counting. The specific activity of ATP in the kinase reaction (e.g., in cpm/pmol) is determined by spotting a small sample of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a GPR1 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., GPR1, sets in motion a cascade of intracellular events, the ultimate consequence of which is a rapid and detectable change in the transcription or translation of one or more genes. The activity of the receptor can therefore be monitored by measuring the expression of a reporter gene driven by control sequences responsive to GPR1 activation.

As used herein "promoter" refers to the transcriptional control elements necessary for receptor-mediated regulation of gene expression, including not only the basal promoter, but also any enhancers or transcription-factor binding sites necessary for receptor-regulated expression.

By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, beta-lactamase or beta-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The transcription factor CREB (cyclic AMP responsive element binding protein) is, as the name implies, responsive to levels of intracellular cAMP. Therefore, the activation of a receptor that signals via modulation of cAMP levels can be monitored by measuring either the binding of the transcription factor, or the expression of a reporter gene linked to a CREB-binding element (termed the CRE, or cAMP response element). Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., Proc. Natl. Acad. Sci., 85: 6662-6666, 1988); the somatostatin gene promoter (cAMP responsive; Montminy et al., Proc. Natl. Acad. Sci., 8.3: 6682-6686, 1986); the proenkephalin promoter (responsive to cAMP, nicotinic agonists, and phorbol esters; Comb et al., Nature, 323: 353-356, 1986); the phosphoenolpyruvate carboxy-kinase (PEPCK) gene promoter (cAMP responsive; Short et al., J. Biol. Chem., 261: 9721-9726, 1986).

Additional examples of transcriptional control elements that are responsive to changes in GPCR activity include, but are not limited to those responsive to the AP-1 transcription factor and those responsive to NF-kB activity.

A given promoter construct should be tested by exposing GPR1-expressing cells, transfected with the construct, to a Humanin polypeptide. An increase of at least two-fold in the expression of reporter in response to Humanin polypeptide indicates that the reporter is an indicator of GPR1 activity.

In order to assay GPR1 activity with a Humanin polypeptide-responsive transcriptional reporter construct, cells that stably express a GPR1 polypeptide are stably transfected with the reporter construct. To screen for agonists, the cells are left untreated, exposed to candidate modulators, or exposed to a Humanin polypeptide, and expression of the reporter is measured. The Humanin polypeptide-treated cultures serve as a standard for the level of transcription induced by a known agonist. An increase of at least 50% in reporter expression in the presence of a candidate modulator indicates that the candidate is a modulator of GPR1 activity. An agonist will induce at least 20%, and preferably the same amount or more, reporter expression than the Humanin polypeptide. This approach can also be used to screen for inverse agonists where cells express a GPR1 polypeptide at levels such that there is an elevated basal activity of the reporter in the absence of Humanin polypeptide or another agonist. A decrease in reporter activity of 10% or more in the presence of a candidate modulator, relative to its absence, indicates that the compound is an inverse agonist.

To screen for antagonists, the cells expressing GPR1 and carrying the reporter construct are exposed to a Humanin polypeptide (or another agonist) in the presence and absence of candidate modulator. A decrease of 10% or more in reporter expression in the presence of candidate modulator, relative to the absence of the candidate modulator, indicates that the candidate is a modulator of GPR1 activity.

Controls for transcription assays include cells not expressing GPR1 but carrying the reporter constructs, as well as cells with a promoterless reporter construct. Compounds that are identified as modulators of GPR1-regulated transcription should also be analyzed to determine whether they affect transcription driven by other regulatory sequences and by other receptors, in order to determine the specificity and spectrum of their activity.

The transcriptional reporter assays, and most cell-based assays, are well suited for screening expression libraries for proteins for those that modulate GPR1 activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue, in the different libraries used for screening of GPR1.

Any of the assays of receptor activity, including the GTP-binding, GTPase, adenylate cyclase, cAMP, phospholipid-breakdown, diacylglycerol, inositol triphosphate, PKC, kinase and transcriptional reporter assays, can be used to determine the presence of an agent in a sample, e.g., a tissue sample, that affects the activity of the GPR1 receptor molecule. To do so, GPR1 polypeptide is assayed for activity in the presence and absence of the sample or an extract of the sample. An increase in GPR1 activity in the presence of the sample or extract relative to the absence of the sample indicates that the sample contains an agonist of the receptor activity. A decrease in receptor activity in the presence of Humanin polypeptide or another agonist and the sample, relative to receptor activity in the presence of Humanin polypeptide alone, indicates that the sample contains an antagonist of GPR1 activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. It is preferred that an agonist stimulates at least 20%, and preferably 75% or 100% or more, e.g., 2-fold, 5-fold, 10-fold or greater receptor activation than Humanin polypeptide.

Other functional assays include, for example, microphysiometer or biosensor assays (Hafner, Biosens. Bioelectron., 15: 149-158, 2000).

II. Diagnostic Assays Based upon the Interaction of GPR1 and Humanin Polypeptide:

Signaling through GPCRs is instrumental in the pathology of a large number of diseases and disorders. GPR1 has been shown to act as a co-receptor for immunodeficiency viruses and can have a role in immune processes, disorders or diseases. The GPR1 expression patterns also suggest that this receptor can play a role in other diseases, disorders or processes, wherein said GPR1-related diseases or GPR1-related disorders are as defined above.

The interaction of GPR1 with Humanin polypeptide can be used as the basis of assays for the diagnosis or monitoring of diseases, disorders or processes involving GPR1 signaling.

Diagnostic assays for GPR1-related diseases, disorders, or processes can have several different forms.

First, diagnostic assays can measure the amount of GPR1 and/or Humanin polypeptide, genes or mRNA in a sample of tissue. Assays that measure the amount of mRNA encoding either or both of these polypeptides also fit in this category.

Second, assays can evaluate the qualities of the receptor or the ligand. For example, assays that determine whether an individual expresses a mutant or variant form of either GPR1 or Humanin polypeptide, or both, can be used diagnostically.

Third, assays that measure one or more activities of GPR1 polypeptide can be used diagnostically.

Therefore, the present invention relates to diagnostic assays for GPR1-related diseases, disorders, or processes. GPR1-related diseases, GPR1-related disorders, or GPR1-related processes might be part from a group as defined above.

The present invention also relates to diagnostic assays for Humanin polypeptide-related diseases, disorders, or processes, wherein said Humanin polypeptide-related diseases or Humanin polypeptide-related disorders are as defined above.

According to the present method, said Humanin polypeptide may be a polypeptide having at least 31% identity, and preferably at least 50%, more preferably at least 75%, most preferably at least 95% and notably 100% identity, to the polypeptide represented by SEQ ID NO: 12; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 12, wherein the fragment retains at least 10% (preferably at least 50%) of the binding activity and/or level of signaling activation of the full length polypeptide of SEQ ID NO: 12. According to the present invention, said Humanin polypeptide may comprise one or more additions, insertions, deletions or substitutions relative to SEQ ID NO: 12. Said Humanin polypeptide may be a truncated Humanin polypeptide; said Humanin polypeptide may be a mutated Humanin polypeptide; said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA tag, Myc tag, FLAG tag) sequences.

According to the present method, said Humanin polypeptide may be a polypeptide having at least 31% identity, and preferably at least 50%, more preferably at least 75%, most preferably at least 95% and notably 100% identity, to the polypeptide represented by SEQ ID NO: 13; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 13, wherein the fragment retains at least 10% (preferably at least 50%) of the binding activity and/or level of signaling activation of the full length polypeptide of SEQ ID NO: 13. According to the present invention, said Humanin polypeptide may comprise one or more additions, insertions, deletions or substitutions relative to SEQ ID NO: 13. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

According to the present method, said Humanin polypeptide may be a polypeptide having at least 31% identity, and preferably at least 50%, more preferably at least 75%, most preferably at least 95% and notably 100% identity, to the polypeptide represented by SEQ ID NO: 14; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 14, wherein the fragment retains at least 10% (preferably at least 50%) of the binding activity and/or level of signaling activation of the full length polypeptide of SEQ ID NO: 14. According to the present invention, said Humanin polypeptide may comprise one or more additions, insertions, deletions or substitutions relative to SEQ ID NO: 14. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA tag, Myc tag, FLAG tag) sequences.

According to the present method, said Humanin polypeptide may be a polypeptide having at least 31% identity, and preferably at least 50%, more preferably at least 75%, most preferably at least 95% and notably 100% identity, to the polypeptide represented by SEQ ID NO: 15; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 15, wherein the fragment retains at least 10% (preferably at least 50%) of the binding activity and/or level of signaling activation of the full length polypeptide of SEQ ID NO: 15. According to the present invention, said Humanin polypeptide may comprise one or more additions, insertions, deletions or substitutions relative to SEQ ID NO: 15. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA tag, Myc tag, FLAG tag) sequences.

A. Assays that Measure the Amount of GPR1 or Humanin Polypeptide

GPR1 and Humanin polypeptide levels can be measured and compared to standards in order to determine whether an abnormal level of the receptor or its ligand is present in a sample, either of which indicates probable dysregulation of GPR1 signaling. Polypeptide levels are measured, for example, by immunohistochemistry using antibodies specific for the polypeptide. A sample isolated from an individual suspected of suffering from a disease or disorder characterized by GPR1 activity is contacted with an antibody for GPR1 or Humanin polypeptide, and binding of the antibody is measured as known in the art (e.g., by measurement of the activity of an enzyme conjugated to a secondary antibody).

Another approach to the measurement of GPR1 and/or Humanin polypeptide levels uses flow cytometry analysis of cells from an affected tissue. Methods of flow cytometry, including the fluorescent labeling of antibodies specific for GPR1 or Humanin polypeptide, are well known in the art.

Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by GPR1 dysregulation.

GPR1 and Humanin polypeptide expression can also be measured by determining the amount of mRNA encoding either or both of the polypeptides in a sample of tissue. mRNA can be quantitated by quantitative or semi-quantitative PCR. Methods of "quantitative" amplification are well known to those of skill in the art, and primer sequences for the amplification of both GPR1 and Humanin polypeptide are disclosed herein. A common method of quantitative PCR involves simultaneously co-amplifying a known quantity of a control sequence using the same primers.

This provides an internal standard that can be used to calibrate the PCR reaction. Detailed protocols for quantitative PCR are provided in PCR Protocols, A Guide to Methods and Applications, Innis et al., Academic Press, Inc. N.Y., (1990), which is incorporated herein by reference. An increase of 10% or more in the amount of mRNA encoding GPR1 or Humanin polypeptide in a sample, relative to the amount expressed in a sample of like tissue from a healthy individual or in a sample of tissue from an unaffected location in an affected individual is diagnostic for a disease or disorder characterized by dysregulation of GPR1 signaling.

B. Qualitative Assays

Assays that evaluate whether or not the GPR1 polypeptide or the mRNA encoding it are wild-type or not can be used diagnostically.

In order to diagnose a disease or disorder characterized by GPR1 or Humanin polypeptide dysregulation in this manner, RNA isolated from a sample is used as a template for PCR amplification of Humanin polypeptide and/or GPR1. The amplified sequences are then either directly sequenced using standard methods, or are first cloned into a vector, followed by sequencing. A difference in the sequence that changes one or more encoded amino acids relative to the sequence of wild-type GPR1 or Humanin polypeptide can be diagnostic of a disease or disorder characterized by dysregulation of GPR1 signaling. It can be useful, when a change in coding sequence is identified in a sample, to express the variant receptor or ligand and compare its activity to that of wild type GPR1 or Humanin polypeptide. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild-type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431. These assays and others known in the art can determine the presence, in a given sample, of a nucleic acid with a known polymorphism.

If desired, array or microarray-based methods can be used to analyze the expression or the presence of mutation, in GPR1 or Humanin polypeptide sequences. Array-based methods for minisequencing and for quantitation of nucleic acid expression are well known in the art.

C. Functional Assays.

Diagnosis of a disease or disorder characterized by the dysregulation of GPR1 signaling can also be performed using functional assays. To do so, cell membranes or cell extracts prepared from a tissue sample are used in an assay of GPR1 activity as described herein (e.g., ligand binding assays, the GTP-binding assay, GTPase assay, adenylate cyclase assay, cAMP assay, phospholipid breakdown, diacyl glycerol or inositol triphosphate assays, PKC activation assay, or kinase assay). The activity detected is compared to that in a standard sample taken from a healthy individual or from an unaffected site on the affected individual. As an alternative, a sample or extract of a sample can be applied to cells expressing GPR1, followed by measurement of GPR1 signaling activity relative to a standard sample. A difference of 10% or more in the activity measured in any of these assays, relative to the activity of the standard, is diagnostic for a disease or disorder characterized by dysregulation of GPR1 signaling.

Modulation of GPR1 Activity in a Cell According to the Invention.

The identification of Humanin polypeptide as a ligand of GPR1 provides methods of modulating the activity of a GPR1 polypeptide in a cell. GPR1 activity is modulated in a cell by delivering to that cell an agent that modulates the function of a GPR1 polypeptide. This modulation can be performed in cultured cells as part of an assay for the identification of additional modulating agents, or, for example, in an animal, including a human. Agents include Humanin polypeptides as defined herein, as well as additional modulators identified using the screening methods described herein.

An agent can be delivered to a cell by adding it to culture medium. The amount to deliver will vary with the identity of the agent and with the purpose for which it is delivered. For example, in a culture assay to identify antagonists of GPR1 activity, one will preferably add an amount of Humanin polypeptide that half-maximally activates the receptors (e.g., approximately $EC_{50}$), preferably without exceeding the dose required for receptor saturation. This dose can be determined by titrating the amount of Humanin polypeptide to determine the point at which further addition of Humanin polypeptide has no additional effect on GPR1 activity.

When a modulator of GPR1 activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) are changed by at least 10% relative to the value for that aspect prior to treatment.

Candidate Modulators Useful According to the Invention.

Candidate modulators can be screened from libraries of synthetic or natural compounds of any size or origin. Numerous means are currently used for random and directed synthesis of saccharide, peptide, lipid, carbohydrate, and nucleic acid based compounds. Synthetic compound libraries of different sizes, including libraries of small organic molecules, may be prepared using well known combinatorial or parallel chemistry techniques or are commercially available from a number of companies. Alternatively, libraries of natural compounds in the form of bacterial, fungal, plant and animal extracts are available from a number of companies, or are readily producible by methods well known in the art. Additionally, natural and synthetically produced libraries and compounds are readily modified through conventional chemical, physical, and biochemical means.

As noted previously herein, candidate modulators can also be variants of known polypeptides (e.g., Humanin polypeptide, antibodies) or nucleic acids (e.g., aptamers) encoded in a nucleic acid library. Cells (e.g., bacteria, yeast or higher eukaryotic cells) transformed with the library can be grown and prepared as extracts, which are then applied in GPR1 binding assays or functional assays of GPR1 activity.

Antibodies Useful According to the Invention.

The invention provides for antibodies to GPR1 and Humanin polypeptide. Antibodies can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., a GPR1 or Humanin polypeptide or an antigenic fragment which is capable of eliciting an antibody response or a fusion protein as described herein above). Immunogens for raising antibodies are prepared by mixing the polypeptides (e.g., isolated recombinant polypeptides or synthetic peptides) with adjuvants. Alternatively, GPR1 or Humanin polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding GPR1 or Humanin polypeptide, or a fragment of these proteins, can be used to express the polypeptides and generate an immune response in an animal as described by Costagliola et al. (J. Clin. Invest., 105: 803-811, 2000). In order to raise antibodies, immunogens are typically administered intradermally, subcutaneously, or intramuscularly to experimental animals such as rabbits, sheep, or mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature, 256: 495-497, 1975)), the human B cell hybridoma technique (Kozbar et al., Immunology Today, 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive with a Humanin polypeptide or GPR1 peptide or polypeptide, and monoclonal antibodies isolated from the media of a culture comprising such hybridoma cells.

Transgenic Animals Useful According to the Invention.

Transgenic animals expressing GPR1 or Humanin polypeptide or variants thereof are useful to study the signaling through GPR1, as well as for the study of drugs or agents that modulate the activity of GPR1. A transgenic animal is a non-human animal containing at least one foreign gene, called a transgene, which is part of its genetic material. Preferably, the transgene is contained in the animal's germ line such that it can be transmitted to the animal's offspring. A number of techniques may be used to introduce the transgene into an animal's genetic material, including, but not limited to, microinjection of the transgene into pronuclei of fertilized eggs and manipulation of embryonic stem cells (U.S. Pat. No. 4,873,191; Palmiter and Brinster, Ann. Rev. Genet., 20: 465-499, 1986; French Patent Application 2593827). Transgenic animals can carry the transgene in all their cells or can be genetically mosaic.

According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Transgenes can be constitutively expressed or can be tissue specific or even responsive to an exogenous drug, e.g., Tetracycline. A transgenic animal expressing one transgene can be crossed to a second transgenic animal expressing a second transgene such that their offspring will carry and express both transgenes.

Knock-Out Animals.

Animals bearing a homozygous deletion in the chromosomal sequences encoding either GPR1 or Humanin polypeptide or variants can be used to study the function of the receptor and ligand. Of particular interest is whether a Humanin knockout has a distinct phenotype, which may point to whether Humanin polypeptide is the only ligand that binds GPR1 or if it is a member of a family. Of further particular interest is the identification of GPR1/Humanin polypeptide in specific physiological and/or pathological processes.

i. Standard Knock Out Animals

Knock out animals are produced by the method of creating gene deletions with homologous recombination. This technique is based on the development of embryonic stem (ES) cells that are derived from embryos, are maintained in culture and have the capacity to participate in the development of every tissue in the animals when introduced into a host blastocyst. A knock out animal is produced by directing homologous recombination to a specific target gene in the ES cells, thereby producing a null allele of the gene. The technology for making knock-out animals is well described (see, for example, Huszar et al., Cell, 88: 131, 1997; and Ohki-Hamazaki et al., Nature, 390: 165, 1997). One of skill in the art can generate a homozygous GPR1 or Humanin polypeptide knock-out animal (e.g., a mouse) using the sequences for GPR1 and Humanin (disclosed herein and known in the art) to make the gene targeting construct.

ii. Tissue Specific Knock Out.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue. In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function. There are now many in vivo examples of this method, including, for instance, the inducible inactivation of mammary tissue specific genes (Wagner et al., Nucleic Acids Res., 25: 4323, 1997). One of skill in the art can therefore generate a tissue-specific knock-out animal in which GPR1 or Humanin is homozygously eliminated in a chosen tissue or cell type.

Kits Useful According to the Invention.

The invention provides for kits useful for screening for modulators of GPR1 activity, as well as kits useful for diagnosis of diseases or disorders characterized by dysregulation of GPR1 signaling. Kits useful according to the invention can include an isolated GPR1 polypeptide (including a membrane- or cell-associated GPR1 polypeptide, e.g., on isolated membranes, cells expressing GPR1, or, on an SPR chip) and an isolated Humanin polypeptide.

A kit can also comprise an antibody specific for GPR1 and/or an antibody for Humanin polypeptide.

Alternatively, or in addition, a kit can contain cells transformed to express a GPR1 polypeptide and/or cells transformed to express a Humanin polypeptide. In a further embodiment, a kit according to the invention can contain a polynucleotide encoding a GPR1 polypeptide and/or a polynucleotide encoding a Humanin polypeptide. In a still further embodiment, a kit according to the invention may comprise the specific primers useful for amplification of GPR1 or Humanin as described below. All kits according to the invention will comprise the stated items or combinations of items and packaging materials therefore. Kits will also include instructions for use.

According to the present kit, said Humanin polypeptide may be a polypeptide having at least 31% identity, and preferably at least 50%, more preferably at least 75%, most preferably at least 95% and notably 100% identity, to the polypeptide represented by SEQ ID NO: 12; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 12, wherein the fragment retains at least 10% (preferably at least 50%) of the binding activity and/or level of signaling activation of the full length polypeptide of SEQ ID NO: 12. According to the present invention, said Humanin polypeptide may comprise one or more additions, insertions, deletions or substitutions relative to SEQ ID NO: 12. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

According to the present kit, said Humanin polypeptide may be a polypeptide having at least 31% identity, and preferably at least 50%, more preferably at least 75%, most preferably at least 95% and notably 100% identity, to the polypeptide represented by SEQ ID NO: 14; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 14, wherein the fragment retains at least 10% (preferably at least 50%) of the binding activity and level of signaling activation of the full length polypeptide of SEQ ID NO: 14. According to the present invention, said Humanin polypeptide may comprise one or more additions, insertions, deletions or substitutions relative to SEQ ID NO: 14. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

According to the present kit, said Humanin polypeptide may be a polypeptide having at least 31% identity, and preferably at least 50%, more preferably at least 75%, most preferably at least 95% and notably 100% identity, to the polypeptide represented by SEQ ID NO: 14; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 14, wherein the fragment retains at least 10% (preferably at least 50%) of the binding activity and level of signaling activation of the full length polypeptide of SEQ ID NO: 14. According to the present invention, said Humanin polypeptide may comprise one or more additions, insertions, deletions or substitutions relative to SEQ ID NO: 14. Said Humanin polypeptide may comprise additional sequences forming a Humanin fusion protein, wherein said additional sequences may be chosen from the group consisting of glutathione-S-transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

According to the present kit, said Humanin polypeptide may be a polypeptide having at least 31% identity, and preferably at least 50%, more preferably at least 75%, most preferably at least 95% and notably 100% identity, to the polypeptide represented by SEQ ID NO: 15; and wherein said polypeptide binds specifically to and activates a signaling activity of a GPR1 polypeptide having the sequence of SEQ ID NO: 2. Alternatively, said Humanin polypeptide may be a fragment of the full length polypeptide of SEQ ID NO: 15, wherein the fragment retains at least 10% (preferably at least 50%) of the binding activity and/or level of signaling activation of the full length polypeptide of SEQ ID NO: 15. According to the present invention, said Humanin polypeptide may comprise one or more additions, insertions, deletions or substitutions relative to SEQ ID NO: 15. Said Humanin polypeptide may comprise additional sequences forming a Humanin polypeptide fusion protein, wherein said additional sequences may be chosen from the group consisting of glutathione-S— transferase (GST), maltose binding protein, alkaline phosphatase, thioredoxin, green fluorescent protein (GFP), histidine tags (e.g., 6× or greater His), or epitope tags (e.g., HA-tag, Myc tag, FLAG tag) sequences.

Biological Assays

In vitro Assay

The modulation of the human GPR1 receptor activity by Humanin polypeptide and Humanin polypeptide derivatives is determined in accordance with the following experimental method.

Experimental Method:

Beta-arrestin2 Recruitment Measurements:

Cells expressing recombinant human GPR1 receptor and the beta-arrestin2 (CHO-K1-hGPR1-Beta-arrestin 2), PathHunter eXpress cells, were plated in OCC2 medium (P/N 30-409), at a density of 20.000 cells/well in a volume of 25 µl in 384-well tissue culture plate. After seeding the cells into the microplates, they were placed into a 37° C., 5% $CO_2$ in a humidified incubator for 24 hours prior to testing. Discard the OCC2 medium and replace it by HBSS 1× (Gibco, 14065), 20 mM HEPES (Gibco, 16530), 0.1% (w/v) BSA (Sigma, A3803), pH 7.4, 20 µl per well. Stock solutions of test compounds were made up at a concentration of 10 mM in DMSO, and serially diluted in HBSS 1× (Gibco, 14065), 20 mM HEPES (Gibco, 16530), 0.1% (w/v) BSA (Sigma, A3803), pH 7.4, to concentrations required for activation dose response curves. Remove the Path Hunter eXpress cells from the incubator and transfer 5 μl from compound plate. Incubate for 90 minutes at 37° C. During the incubation period, prepare a working solution of the detection reagents for each 384-well plate by mixing the following reagents: Cell Assay Buffer (19 parts), Substrate reagent 1 (5 parts), and Substrate Reagent 2 (1 part). Add 12.5 μl of prepared detection reagent per well and incubate for 90 minutes at room temperature (23° C.). Read samples on standard luminescence plate reader (Fluostar), under the following conditions: measurement interval: 0.1 second, interval time: 0.1 second, number of interval: 1, gain: auto-adjustment, emission filter: lens. Raw data were analysed with GrphPad Prism software for curve drawing and $EC_{50}$ calculation.

Agonistic activities ($EC_{50}$ values) of all exemplified compounds are in the range of 46-93 nM with an average of 64 nM with respect to GPR1 receptor. Agonistic activities of selected compounds are displayed in Table 1. Compounds mentioned in Table 1 are commercially available.

TABLE 1

| Compound | $EC_{50}$ [nM] |
|---|---|
| Humanin | 60.9 |
| Gly14-Humanin | 46.1 |
| d-Ser14-Humanin | 92.8 |
| Ala8-Humanin | 55.6 |

ABBREVIATIONS

BSA: Bovine Serum Albumin
cAMP: Cyclic Adenosine MonoPhosphate
CAT: Chloramphenicol AcetylTransferase
CDR: Complementarity-Determining Region
CRE: cAMP Response Element
CRE: Cyclization Recombination
DAG: DiAcylGlycerol
DMSO: Dimethylsulfoxide
EGTA: Ethylene Glycol-bis(beta-aminoethyl ether)-N,N,N', N'-Tetra Acetic acid
ELISA: Enzyme-Linked Immunosorbent Assay
FLP: FLiPpase Recombinase Enzyme
FPRL1: Formyl Peptide Receptor Like 1
FPRL2: Formyl peptide Receptor Like 2
FRET: Fluorescence Energy Transfer
GDP: Guanosine DiPhosphate
GPCR: G Protein Coupled Receptor
GPR1 G Protein Coupled Receptor 1
GTP: Guanosine TriPhosphate
HBSS: Hanks Balanced Salt Solution
HEPES: 4-(2-HydroxyEthyl)-1-piperazineEthaneSulfonic acid
HIV: Human Immunodeficiency Virus
HN: Humanin
Kd: Equilibrium Constant for Dissociation
PCR: Polymerase Chain Reaction
RT/PCR: Reverse Transcriptase/polymerase Chain reaction
RLU Relative Light Units
SIV: Simian Immunodeficiency Virus

The invention claimed is:

1. A method of identifying an agent that modulates the function of GPR1, the method comprising:
   a) contacting a GPR1 polypeptide with a Humanin polypeptide in the presence or absence of a candidate modulator under conditions permitting the interaction of the Humanin polypeptide with the GPR1 polypeptide; and
   b) measuring the interaction of the GPR1 polypeptide with the Humanin polypeptide, wherein an increase or a decrease in interaction in the presence of the candidate modulator, relative to the interaction in the absence of the candidate modulator, identifies the candidate modulator as an agent that modulates the function of GPR1; wherein the Humanin polypeptide is a polypeptide having at least 95% sequence identity to polypeptides of SEQ ID NO: 12, 13, 14 or 15 that specifically binds to and/or activates a signaling activity of a GPR1 polypeptide having the sequence of SEQ ID NO: 2.

2. A method of identifying an agent that modulates the function of GPR1, the method comprising:
   a) contacting a GPR1 polypeptide with a Humanin polypeptide in the presence or absence of a candidate modulator under conditions permitting the interaction of the Humanin polypeptide with the GPR1 polypeptide; and
   b) measuring a signaling activity of the GPR1 polypeptide, wherein a change in the activity in the presence of the candidate modulator relative to the activity in the absence of the candidate modulator identifies the candidate modulator as an agent that modulates the function of GPR1; wherein the Humanin polypeptide is a polypeptide having at least 95% sequence identity to polypeptides of SEQ ID Nos: 12, 13, 14 or 15 that specifically binds to and/or activates a signaling activity of a GPR1 polypeptide having the sequence of SEQ ID No: 2.

3. A method of identifying an agent that modulates the function of GPR 1, the method comprising:
   a) contacting a GPR1 polypeptide with a candidate modulator;
   b) measuring a signaling activity of the GPR1 polypeptide in the presence of the candidate modulator; and
   c) comparing the activity measured in the presence of the candidate modulator to the activity measured in a sample in which the GPR1 polypeptide is contacted with a Humanin polypeptide, wherein the candidate modulator is identified as an agent that modulates the function of GPR1 when the amount of the activity measured in the presence of the candidate modulator is at least 50% of the amount induced by the Humanin polypeptide present at its $EC_{50}$;
wherein the Humanin polypeptide is a polypeptide having at least 95% identity to polypeptides of SEQ ID NOs: 12, 13, 14 or 15 that specifically binds to and/or activates a signaling activity of a GPR1 polypeptide having the sequence of SEQ ID NO: 2.

4. The method according to claim 1, wherein said agent that modulates the function of GPR1 is present in a sample.

5. The method according to claim 1, wherein the measurement is performed using a method selected from label displacement, surface plasmon resonance, fluorescence resonance energy transfer, fluorescence quenching, or fluorescence polarization.

6. The method according to claim 1, wherein said GPR1 polypeptide sequence is SEQ ID NO: 2, wherein and said Humanin polypeptide sequence is SEQ ID NO: 12, and wherein said Humanin polypeptide binds specifically to said GPR1 polypeptide.

7. The method according to claim 1, wherein said Humanin polypeptide sequence is selected from SEQ ID NO: 12, SEQ ID NO.: 13, SEQ ID NO: 14, or SEQ ID NO: 15.

8. The method according to claim 1, wherein the Humanin polypeptide is delectably labeled.

9. The method according to claim 1, wherein the GPR1 polypeptide is expressed in or on a cell.

10. The method according to claim 1, wherein the GPR1 polypeptide is present in a cell membrane.

11. The method according to claim 9, wherein said cell is selected from COS-7-cells, a CHO cell, a U20S cell, a LM (TK-) cell, a NIH-3T3 cell, a HEK cell, a K-562 cell, or an 1321 N 1 astrocytoma cell.

12. The method according to claim 1, wherein the GPR1 polypeptide is present in or on synthetic liposomes or virus-induced budding membranes.

13. The method according to claim 3, wherein the method is further performed in the presence of Gα16.

14. The method according to claim 1, wherein the agent is selected from a peptide, a polypeptide, an antibody or antigen-binding fragment thereof, a lipid, a carbohydrate, a nucleic acid, or a small organic molecule.

15. The method according to claim 2, wherein the step of measuring a signaling activity comprises measurement of guanine nucleotide binding or exchange, adenylate cyclase activity, cAMP, beta-arrestin 1 recruitment, beta-arrestin 2 recruitment, Protein Kinase C activity, phosphatidylinositol breakdown, diacylglycerol, inositol triphosphate, intracellular calcium, arachidonic acid, MAP kinase activity, tyrosine kinase activity, or reporter gene expression.

16. The method according to claim I, wherein measuring the interaction of the GPR1 polypeptide with the Humanin polypeptide with the candidate modulator is measured relative to the interaction in the absence of the candidate modulator.

17. The method according to claim 2, wherein said GPR1 polypeptide sequence is SEQ ID NO: 2, wherein said Humanin polypeptide sequence is SEQ ID NO: 12, and wherein said Humanin polypeptide binds specifically to said GPR1 polypeptide.

18. The method according to claim 3, wherein said GPR1 polypeptide sequence is SEQ ID NO: 2, wherein said Humanin polypeptide sequence is SEQ ID NO: 12, and wherein said Humanin polypeptide binds specifically to said GPR1 polypeptide.

19. The method according to claim 2, wherein said Humanin polypeptide sequence is SEQ ID NO: 12, SEQ ID NO: 13, SEQ ID NO: 14 or SEQ ID NO: 15.

20. The method according to claim 3, wherein said Humanin polypeptide sequence is SEQ ID NO: 12, SEQ ID NO: 13, SEQ ID NO: 14 or SEQ ID NO: 15.

21. The method according to claim 2, wherein the GPR1 polypeptide is expressed in or on a cell.

22. The method according to claim 3, wherein the GPR1 polypeptide is expressed in or on a cell.

23. The method according to claim 6, wherein the GPR1 polypeptide is expressed in or on a cell.

24. The method according to claim 2, wherein the GPR1 polypeptide is present in a cell membrane.

25. The method according to claim 3, wherein the GPR1 polypeptide is present in a cell membrane.

26. The method according to claim 6, wherein the GPR1 polypeptide is present in a cell membrane.

27. The method according to claim 2, wherein the GPR1 polypeptide is present in or on synthetic liposomes or virus-induced budding membranes.

28. The method according to claim 3, wherein the GPR1 polypeptide is present in or on synthetic liposomes or virus-induced budding membranes.

29. The method according to claim 6, wherein the GPR1 polypeptide is present in or on synthetic liposomes or virus-induced budding membranes.

30. The method according to claim 2, wherein the agent is a peptide, a polypeptide, an antibody or antigen-binding fragment thereof, a lipid, a carbohydrate, a nucleic acid, or a small organic molecule.

31. The method according to claim 3, wherein the agent is a peptide, a polypeptide, an antibody or antigen-binding fragment thereof, a lipid, a carbohydrate, a nucleic acid, or a small organic molecule.

32. The method according to claim 3, wherein the step of measuring a signaling activity comprises measurement of guanine nucleotide binding or exchange, adenylate cyclase activity, cAMP, beta-arrestin 1 recruitment, beta-arrestin 2 recruitment, Protein Kinase C activity, phosphatidylinositol breakdown, diacylglycerol, inositol triphosphate, intracellular calcium, arachidonic acid, MAP kinase activity, tyrosine kinase activity, or reporter gene expression.

* * * * *

UNITED STATES PATENT AND TRADEMARK OFFICE
CERTIFICATE OF CORRECTION

| | | |
|---|---|---|
| PATENT NO. | : 8,709,734 B2 | Page 1 of 1 |
| APPLICATION NO. | : 13/499896 | |
| DATED | : April 29, 2014 | |
| INVENTOR(S) | : Xavier Leroy | |

It is certified that error appears in the above-identified patent and that said Letters Patent is hereby corrected as shown below:

On the Title Page: Item (30) add as follows:

(30)    Foreign Application Priority Data

Oct. 2, 2009    (IB) ........................ PCT/IB2009/054324

Signed and Sealed this
Twenty-second Day of July, 2014

Michelle K. Lee
*Deputy Director of the United States Patent and Trademark Office*